US005683868A

United States Patent [19]
LaRossa et al.

[11] Patent Number: 5,683,868
[45] Date of Patent: Nov. 4, 1997

[54] HIGHLY SENSITIVE METHOD FOR DETECTING ENVIRONMENTAL INSULTS

[75] Inventors: Robert Alan LaRossa, West Chester, Pa.; William Robert Majarian, Mount Royal, N.J.; Tina Kangas Van Dyk, Wilmington, Del.

[73] Assignee: E. I. Du Pont de Nemours and Company, Wilmington, Del.

[21] Appl. No.: 244,376

[22] PCT Filed: Dec. 2, 1993

[86] PCT No.: PCT/US93/11527

§ 371 Date: Oct. 6, 1994

§ 102(e) Date: Oct. 6, 1994

[87] PCT Pub. No.: WO94/13831

PCT Pub. Date: Jun. 23, 1994

Related U.S. Application Data

[63] Continuation-in-part of Ser. No. 63,173, May 14, 1993, abandoned, which is a continuation-in-part of Ser. No. 988,428, Dec. 4, 1992, abandoned.

[51] Int. Cl.⁶ ............... C12Q 1/68; C12N 1/21; C07H 21/04
[52] U.S. Cl. .................. 435/6; 435/8; 435/29; 435/252.33; 536/23.2; 536/23.7; 536/24.1
[58] Field of Search .................. 435/6, 8, 29, 172.1, 435/172.3, 252.3, 252.33, 320.1; 536/23.1, 23.7, 24.1, 23.2

[56] References Cited

U.S. PATENT DOCUMENTS

| | | | |
|---|---|---|---|
| 4,581,335 | 4/1986 | Baldwin | 435/172.3 |
| 5,221,623 | 6/1993 | Legocki et al. | 435/252.3 |

FOREIGN PATENT DOCUMENTS

| | | | |
|---|---|---|---|
| WO 90/02947 | 3/1990 | WIPO | G01N 33/00 |
| WO 90/04037 | 4/1990 | WIPO | C12Q 1/18 |
| WO 90/08836 | 8/1990 | WIPO | C12Q 1/02 |
| WO 92/15687 | 9/1992 | WIPO | C12N 15/62 |
| WO 93/03179 | 2/1993 | WIPO | C12Q 1/66 |
| WO 94/01584 | 1/1994 | WIPO | C12Q 1/68 |

OTHER PUBLICATIONS

VanBogelen, R. et al, *J. of Bacteriology*, 169(1), 26–32 (1987).
Bains, W., *Biotechnology*, 10, 515–518 (1992).
LaRossa, R. et al, *Molecular Microbiology*, 5(3), 529–534 (1991).
Blom, A. et al, *Applied and Environmental Microbiology*, 58(1), 331–334 (1992).
Tatsumi, H. et al, *Biochimica et Biophysica Acta*, 1131, 161–165 (1992).
Jacobs, M. et al, *Mol. Gen. Genet*, 230, 251–256(1991).
Burlage, R. et al, *J. of Bacteriology*, 172(9), 4749–4757 (1990).
Anderson, R., *New Scientist*, pp. 50–52, Apr. 1, 1989.
Park, S.F. et al, *J. of General Microbiology*, 138, 2619–2627 (1992).
Gomes, S.L. et al, *Bacteriol.*, 172(6), 3051–3059 (1990).
Dutton, R.J. et al, *Toxic Assess*, 5(3), 253–264 (1990).

*Primary Examiner*—David Guzo

[57] ABSTRACT

Subtle changes in environmental stress can now be detected and measured at sublethal levels as a generic response to environmental stress. The present invention provides a method to detect changes in the environmental stress level. The stress change is indicated as a change in the luminescence output of a genetically engineered microorganism. In the present invention, the luminescence gene complex is under the control of a stress inducible promoter.

13 Claims, 8 Drawing Sheets

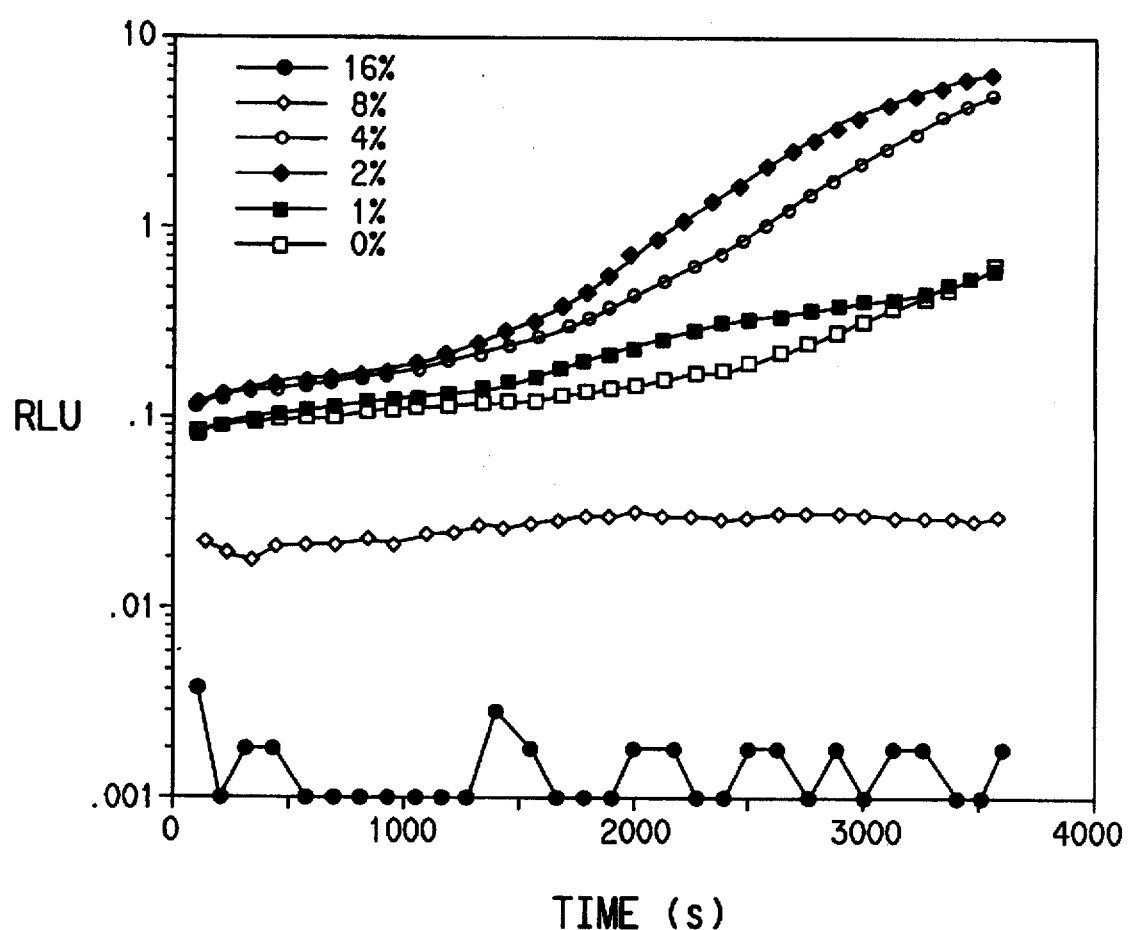

SEQUENCE LISTING ( 1 ) GENERAL INFORMATION:

( i i i ) NUMBER OF SEQUENCES: 24

( 2 ) INFORMATION FOR SEQ ID NO:1:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

GTTAGCGGAT CCAAAAGCAC AAAAAAT    27

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

AGCAGTGAAT TCCATCTAAA CGTCTCCA    28

( 2 ) INFORMATION FOR SEQ ID NO:3:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ACTTAAGGAT CCAAGCGATG GCGCGTAAAA    30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

AGCAGCGAAT TCATCGCCGC TTCCAGACAA    30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

ACTTAAGGAT CCAGAGAAGC CTGTCGGCAC                              30

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AGCTTTGAAT TCCGCTTCTG TTTGTTTT                                28

( 2 ) INFORMATION FOR SEQ ID NO:7:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ACTTTTGGAT CCGTGTAAAC GCGCGATTG                               29

( 2 ) INFORMATION FOR SEQ ID NO:8:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

AGCAGCGAAT TCTTCCCGGA TTAAACGCTT                              30

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ACTTAAGGAT CCCGAAATGA GGGCGGGAAA                              30

( 2 ) INFORMATION FOR SEQ ID NO:10:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

AGCAGCGAAT TCGAACGTTG CTGACCACGA                              30

( 2 ) INFORMATION FOR SEQ ID NO:11:

( i ) SEQUENCE CHARACTERISTICS:
    ( A ) LENGTH: 30 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:11:

ACTTAAGGAT CCCCCAAAA ATGCAGAATA                       30

( 2 ) INFORMATION FOR SEQ ID NO:12:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

AGCAGCGAAT TCGGGCATCC GGTTGAAATA G                     31

( 2 ) INFORMATION FOR SEQ ID NO:13:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:13:

ACTTAAGGAT CCGCCATTAC GTTGGCTGAA                       30

( 2 ) INFORMATION FOR SEQ ID NO:14:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

AGCAGCGAAT TCCCACCCGT TTCGGTCATT                       30

( 2 ) INFORMATION FOR SEQ ID NO:15:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:15:

ACTTAAGGAT CCCTCCCGAT ACGCTGCCA                        29

( 2 ) INFORMATION FOR SEQ ID NO:16:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear -continued (i i) MOLECULE TYPE: DNA (genomic)

(x i) SEQUENCE DESCRIPTION: SEQ ID NO:16:

AGCAGCGAAT TCGGCGATGA GAATGTGTTT AT    32

(2) INFORMATION FOR SEQ ID NO:17:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:17:

ACTTAAGGAT CCAATTACTG CGCCATTCTG    30

(2) INFORMATION FOR SEQ ID NO:18:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:18:

ACATCGGAAT TCTCATAGTC GCTGCCATTT    30

(2) INFORMATION FOR SEQ ID NO:19:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:19:

ACTTAAGGAT CCCTAATTGT ACGCATGTCA    30

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:20:

AGCAGCGAAT TCAAAGTCTC TGTGAATGTT    30

(2) INFORMATION FOR SEQ ID NO:21:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (i i) MOLECULE TYPE: DNA (genomic)

(x i) SEQUENCE DESCRIPTION: SEQ ID NO:21:

```
ACTTAAGGAT CCAGATTATC GTCACTGCAA                                    30
```

( 2 ) INFORMATION FOR SEQ ID NO:22:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:22:

```
AGCAGCGAAT TCGGCCAATC AGCAAAATAA                                    30
```

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:23:

```
ACTTTCGGAT CCTTGGTGCA ACATTCACAT                                    30
```

( 2 ) INFORMATION FOR SEQ ID NO:24:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:24:

```
AGCAGCGAAT TCTCAGCGGA CATCGTCAGT                                    30
```

HIGHLY SENSITIVE METHOD FOR DETECTING ENVIRONMENTAL INSULTS

CROSS-REFERENCE TO RELATED APPLICATIONS.

This application claims the benefit of the following prior-filed or national or international applications. This application is a national filing of PCT/US93/11527, Internt'l Filing Date 2 Dec. 1993, which in turn is a continuation-in-part of U.S. application Ser. No. 08/063,173, filed 14 May 1993, (now abandoned), which in turn is a continuation-in-part of U.S. application Ser. No. 07/988,428, filed 4 Dec. 1992, (now abandoned).

FIELD OF INVENTION

The invention relates to the detection of environmental insults at levels below those necessary to compromise cell metabolism. More specifically the invention provides a transformed bacterial host containing a DNA construct comprising a stress inducible promoter operably connected to a reporter gene or gene complex such that the presence of an environmental insult will induce the expression of the reporter genes. The preferred reporter genes are those that are responsible for bacterial bioluminescence.

BACKGROUND

Increasing public concern and mounting government regulations have provided impetus for the development of environmental sensing systems capable of detecting contaminants in soil and ground water. Highly sensitive and specific detection systems incorporating analytical tools such as Gas Chromatography and Mass spectrophotometry have been known for several years; however, these systems require expensive equipment and skilled operators. Moreover, sample preparation and data analysis is often cumbersome and time consuming. Toxicity assays involving living organisms such as Daphnia, used in the standard U.S. water toxicity test, are simpler; however, these tests are non-specific and not particularly rapid. Somewhat more rapid are cell based toxicity assays that incorporate a bacterial cell as the sensitive element. These systems use bacterial cells as a reagent in a conventional automated analytical system. For example the RODTOX system (Central Kagaku., Tokyo, Japan) is a batch assay that measures bacterial oxygen consumption and was designed for use in sewage plants. Other bacteria based systems such as the GBI TOXALARM system (Genossenschaft Berliner Ingenieuirkollective, Berlin, Germany) can measure the presence of specific chemicals. The GBI TOXALARM is known to be able to detect the presence of as little as 0.1 ppm potassium cyanide in a sample. These detection systems are useful, but are hampered by cumbersome and complex detection systems. Recently, the phenomenon of bacterial bioluminescence has been regarded as providing a simpler and more sensitive mode of detection in environmental sensing systems.

The phenomenon of bioluminescence first came under serious scientific scrutiny by Raphel Dubois in 1885 when he observed that the cell-free extracts obtained from the luminescent beetle Pyrophrus and the luminescent clam Pholas gave a light emitting reaction in vitro when mixed at room temperature. Since that time bioluminescent systems have been identified and examined in a myriad of different organisms including the common firefly, marine coelenterates, fish, terrestrial and freshwater worms, as well as bacterial, algal and fungal species.

Bacterial bioluminescence is phenomenon in which the products of 5 structural genes (luxA, luxB, luxC, luxD and luxE) work in concert to produce light. The luxD product generates a C14 fatty acid from a precursor. The C14 fatty acid is activated in an ATP dependent reaction to an acyl-enzyme conjugate through the action of the luxE product which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the C14 aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

Recently, naturally bioluminescent organisms have been used as the sensitive element in toxicity tests. The MICROTOX system, (Microbics Corp., Carlsbad, Calif.) is an example. The MICROTOX system measures the natural baseline luminescence of *Photobacterium phosporeum* and relates this to the hostility of the environment around the organism. Since the three couples, ATP level, NADPH level and $FMNH_2$ level, between light production and the central metabolic events of energy generation are necessary for light production in *Photobacterium phosporeum*, any insult that interferes with the availability or interaction of these metabolites will cause a decrease in the activity of the bioluminescence(lux) system and therefore a related decrease in light production by the organism.

A main attribute of bioluminescent systems is that the decrease in light production is rapid, occuring within minutes of exposure to an insult. Another key advantage of these systems is that light detection can be exquisitely sensitive (down to the level of single photons), and is readily adaptable to portable field units. Furthermore, the logistics of light detection precludes the necessity of having the detector contact a wet, biological sample, which is a key weakness in competing technologies (such as ion-selective electrodes), where detector fouling and corrosion are responsible for significant down time.

Recent advances in recombinant DNA technology have made it possible to express the luciferase (lux) gene complex as heterologous gene products. This is generally accomplished by placing the lux structural gene complex under the control of a host promoter. So, for example cDNA encoding firefly luciferase has been expressed in *E. coli* under the control of the lacZ promoter. (Tatsumi et al., Biochem. Biophys Acta., 1131, (2), pp 161–165, (1992)), and the luxAB fusion gene has been expressed in Bacillus at levels comparable to those achievable in *E. coli* by placing it under the control of the powerful Pxyn promoter (Jacobs et al., *Mol. Gen. Genet.*, 230(1–2), pp 251–256, (1991)).

Alternate systems to the MICROTOX system have been developed using recombinant genetics to transform bacteria to be the light emitting element in the assay. Rychert et al. (*Environ. Toxic. Water Qual.*, 6 (4), pp 415–422, (1991)) have shown that recombinant *E. coli* harboring the plasmid, pJE202, that contain the lux gene complex, was sensitive to $Zn^{2+}$, ethidium bromide, sodium pentachoropheate, $Cu^{2+}$ and 2,4-dichloropheoxyacetic acid. Response in this assay was registered by a decrease in baseline light emitted by the transformed *E. coli*.

Although the MICROTOX and similar systems are useful, their sensitivity is limited to detecting levels of insults that kill or cripple the cell metabolically. To be detected by these systems, the insult must have reached a level high enough to either interfere with the central metabolism of the cell or to inactivate the Lux proteins.

Frequently it is necessary to be able to detect levels of insults at levels below those needed to affect cell metabolism. Such is the case in waste treatment facilities where lethal concentrations of pollutants can eradicate the useful microbial population, incurring significant cost and plant down time. A preferred sensing system would be one that would be able to detect the presence of insults at sublethal levels, before a useful microbial population could be harmed. Such an early warning could be used to trigger prompt remedial action to save the indigenous microbial population.

Recently, recombinant bacteria have been developed by fusing the lux structural genes to chemically responsive bacterial promoters and then placing such chimeras in appropriate hosts. These recombinant bacteria are sensor organisms that glow in response to specific stimuli. An example of this type of gene fusion is described by Burlage et al. (*J. Bacteriol*, 172 (9) pp 4749–4757 (1990)) where a DNA fragment from plasmid NAH7 containing a promoter for the naphthalene degradation pathway was fused to the lux genes of *Vibrio fischeri* and used to transform a strain of Pseudomonas. The resulting transformant displayed an increase in light emission in the presence of naphthalene. The induction of bioluminescence was demonstrated to coincide with naphthalene degradation by the transformed organism.

Another test system specifically responsive to mercury (Hg) is described by H. Molders (EP 456667). Here, indicator bacterial strains are provided (by vector mediated gene transfer) containing a met promoter, specifically inducible by Hg ions, fused to a bacterial luciferase (lux AB) genes complex which is responsible for bioluminescence. The test system of Molders relies on the induction of the met promoter by the presence of mercury and the subsequent increase in light emission from the recombinant bacteria for the test results.

The methods of Burlage et al. and Molders offer several advantages over the art in that they specifically detect a single insult by the method of increased bioluminescence. These systems are useful for detecting the presence of specific chemicals in an environmental sample but are poor indicators of general cell toxicity. The promoter used by Burlage is functional in the naphthalene degradative pathway and is placed in a host that is able to use naphthalene as a carbon source. Hence this detection system is not associated with cell toxicity in any way. Similarly the mer-promoter of Molders is not indigenous to *E. coli* and therefore is not a native indicator of toxicity in *E. coli*. A more general test system for the primary detection of unknown insults would utilize a promoter specifically linked to cell toxicity or stress rather than one activated by one specific chemical.

Genes activated as a result of cellular stress provide an advantageous alternative strategy for the detection of environmental insults. Stress genes are found in all cells and are defined as those genes activated as a result of any type of stress that might alter the normal cellular metabolism. Environmental stresses often induce synthesis of an overlapping set of proteins. The most well recognized class of stress genes are the heat shock genes encoding a set of cellular proteins thought to have roles in refolding, recycling and resynthesis of proteins. The heat shock phenomenon was first described as a response to an increased temperature. Subsequent work has shown that exposure to a variety of stresses including phage infection, macrophage envelopment, as well as the presence of organic molecules and heavy metals can also trigger the heat shock response. The common theme of the inducing agents may be unfolding of some proteins within the cell. (LaRossa et al., *Mol. Micriobiol.*, 5(3), pp 529–534, (1991)). Thus the response may integrate and report a wide range of environmental insults. VanBogelen et al. (*J. Bacteriol*, 169(1), pp 26–32, (1987)) have demonstrated that a variety of chemicals are able to induce the heat shock genes in *E. coli*, including $CdCl_2$, $H_2O_2$, ethanol, puromycin and nalidixic acid. Blom et al. (*Appl. Environ. Microbiol.*, 58(1), pp 331–334, (1992)) teach that the exposure of *E. coli* cultures to benzene, $CdCl_2$, chlorpyrivos, 2,4-dichloraniline, dioctylphtalate, hexachlorobenzene, pentachlorophenol, trichloroethylene, and tetrapropylbenzosulfonate leads to the induction of up to 39 different stress proteins, as analyzed by two dimensional gel electrophoresis.

Since the cell attempts to maintain a steady state, stress responses are activated well below the minimal inhibitory concentration for any condition that serves as a triggering factor. This fact would make the use of stress responses in any environmental monitoring system particularly advantageous since detection of insults could be accomplished before microbial cell death. Such a system would be extremely useful in waste treatment facilities where environmental pollutants are often not detected until after the microbial population has been destroyed.

To date the induction of stress responses has been utilized in the area of environmental testing with only moderate success. Koehler et al. (*Arch. Environ. Contam. Toxicol.*, 22(3), 334–8, (1992)) describe a test system to assay the levels of HSP70 protein in various species of molluscs and slugs in response to the presence of heavy metals and pesticides. Although the system demonstrated increased levels of HSP70 in response to the presence of $Pb^{2+}$, the technique is cumbersome and lacks sensitivity. A more sophisticated technique described is by Saunders et al. (WO 9002947). The Saunders et al. technique involves detecting increased levels of HSP60 and HSP70 in organisms exposed to pollutants in an aqueous environment.

Although stress responses have been demonstrated to be useful in detecting the presence of various environmental insults, it has yet to be linked to a sensitive, easily detected reporter. A need exists, therefore for a highly sensitive biological test system employing a facile detection mechanism, able to detect a wide variety of insults at levels well below those needed to kill microbial populations. It is the object of the present invention to meet such a need. This invention is anticipated to have broad applicability. Potential uses include monitoring of air and water quality, agrichemical and pharmaceutical design, manufacturing and fermentation process control, process monitoring and toxicity screening. These applications may benefit many enterprises including the chemical, beverage, food and flavor, cosmetics, agricultural, environmental, regulatory and health care industries.

SUMMARY OF THE INVENTION

The present invention provides a method for detecting the presence of an environmental insult comprising the steps of: culturing a suitable bioluminescent detector organism capable of responding to the presence of an environmental insult by a change in luminescence; exposing said detector organism to the presence of a sample suspected of containing an environmental insult; measuring the change in luminescence produced by the detector organism; and correlating said change in luminescence with the level of environmental insult present in said sample.

The present invention further provides a transformed bioluminescent bacterial host cell capable of a change in luminescence in response to the presence of an environmental insult, wherein said host cell contains a heterologous DNA construct capable of being activated by the presence of said insult.

Additionally the present invention provides a DNA fusion comprising a first DNA fragment encoding a stress inducible promoter, operably and expressibly connected to a second DNA fragment encoding the lux gene complex.

BRIEF DESCRIPTION OF THE DRAWINGS
AND BIOLOGICAL DEPOSITS

FIG. 6b is a graphic representation of the increase in luminescence by WM1026 in response to the presence of varying concentrations of ethanol.

Figure 1:
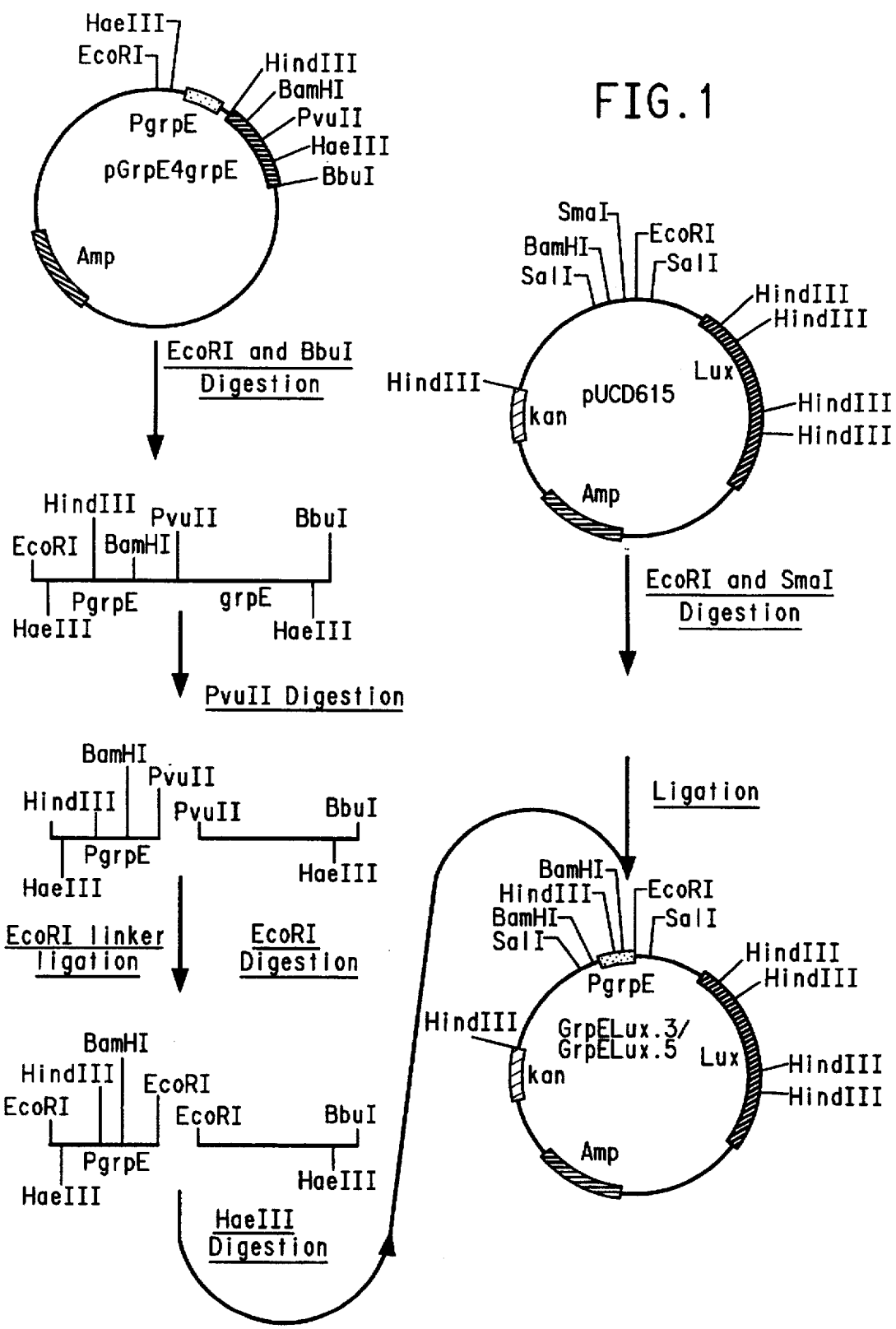
FIG. 1 is an illustration of the construction of plasmid pGrpELux.3 and pGrpELux.5.

The following strains were deposited under the terms of the Budapest Treaty with the American Type Culture Collection (ATCC) (12301 Packlawn Drive, Rockville, Md. 20852, U.S.A.):

| TV1060 (ATCC #69142)* | WM1202 (ATCC #69313)* |
| TV1061 (ATCC #69315)* | WM1021 (ATCC #69141)† |
| TV1076 (ATCC #69314)* | WM1026 (ATCC #69143)† |
|                       | WM1302 (ATCC #69316)* |

(*deposited 13 May 1993)
(†deposited 3 December 1992)

DETAILED DESCRIPTION OF THE INVENTION

The following definitions are used herein and should be referred to for claim interpretation.

The terms "promoter" and "promoter region" refer to a sequence of DNA, usually upstream of (5' to) the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

A "fragment" constitutes a fraction of the DNA sequence of the particular region.

"Nucleic acid" refers to a molecule which can be single stranded or double stranded, composed of monomers (nucleotides) containing a sugar, phosphate and either a purine or pyrimidine. In bacteria and in higher plants, "deoxyribonucleic acid" (DNA) refers to the genetic material while "ribonucleic acid" (RNA) is involved in the translation of the information from DNA into proteins.

"Regulation" and "regulate" refer to the modulation of gene expression controlled by DNA sequence elements located primarily, but not exclusively upstream of (5' to) the transcription start of a gene. Regulation may result in an all or none response to a stimulation, or it may result in variations in the level of gene expression.

The term "coding sequence" refers to that portion of a gene encoding a protein, polypeptide, or a portion thereof, and excluding the regulatory sequences which drive the initiation of transcription. A coding sequence may be one normally found in the cell or it may be one not normally found in a cellular location wherein, it is introduced, in which case it is termed a heterologous gene. The coding sequence may be a composite of segments derived from different sources, naturally occurring or synthetic.

The term "construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

The term "transformation" refers to the acquisition of new genes in a cell after the incorporation of nucleic acid.

The term, "operably linked" refers to the fusion of two fragments of DNA in a proper orientation and reading frame to be transcribed into functional RNA.

The term "expression" refers to the transcription and translation to gene product from a gene coding for the sequence of the gene product. In the expression, a DNA chain coding for the sequence of gene product is first transcribed to a complimentary RNA which is often a messenger RNA and, then, the thus transcribed messenger RNA is translated into the above-mentioned gene product if the gene product is a protein.

The term "translation initiation signal" refers to a unit of three nucleotides (codon) in a nucleic acid that specifies the initiation of protein synthesis.

The term "plasmid" as used herein refers to an extra chromosomal element often carrying genes which are not part of the central metabolism of the cell, and usually in the form of circular double-stranded DNA molecules.

The term "restriction endonuclease" refers to an enzyme which binds and cuts within a specific nucleotide sequence within double-stranded DNA.

The term "bioluminescence" refers to the phenomenon of light emission from any living organism.

The term "lux" refers to the lux structural genes which include luxA, luxB, luxC, luxD and luxE and which are responsible for the phenomenon of bacterial bioluminescence. A lux gene complex might include all of the independent lux genes, acting in concert, or any subset of the lux structural genes so long as luxA and luxB are part of the complex.

The term "stress" or "environmental stress" refers to the condition produced in a cell as the result of exposure to an environmental insult.

The term "insult" or "environmental insult" refers to any substance or environmental change that results in an alteration of normal cellular metabolism in a bacterial cell or population of cells. Environmental insults may include, but are not limited to, chemicals, environmental pollutants, heavy metals, changes in temperature, changes in pH as well as agents producing oxidative damage, DNA damage, anaerobiosis, changes in nitrate availability or pathogenesis.

The term "stress response" refers to the cellular response resulting in the induction of either detectable levels of stress proteins or in a state more tolerant to exposure to another insult or an increased dose of the environmental insult.

The term "stress protein" refers to any protein induced as a result of environmental stress or by the presence of an environmental insult. Typical stress proteins include, but are not limited to those encoded by the Escherichia coli genes groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA and fabA.

The term "stress gene" refers to any gene whose transcription is induced as a result of environmental stress or by the presence of an environmental insult. Typical E. coli stress genes include, but are not limited to groEL, groES, dnaK, dnaJ, grpE, lon, lysU, rpoD, clpB, clpP, uspA, katG, uvrA, frdA, sodA, sodB, soi-28, narG, recA, xthA, his, lac, phoA, glnA, micF, and fabA.

The term "heat shock gene" refers to any gene for which its synthesis is positively controlled by the structural gene encoding the sigma-32 protein (rpoH).

The term "stress inducible promoter" refers to any promoter capable of activating a stress gene and causing increased expression of the stress gene product.

The term "detector organism" refers to an organism which contains a gene fusion consisting of a stress inducible promoter fused to a structural gene and which is capable of expressing the lux gene products in response to an environmental insult. Typical detector organisms include but are not limited to bacteria.

The term "log phase" or "log phase growth" refers to cell cultures of detector organisms growing under conditions permitting the exponential multiplication of the detector cell number.

The term "Relative Light Unit" is abbreviated "RLU" and refers to a measure of light emission as measured by a luminometer, calibrated against an internal standard unique to the luminometer being used.

The designation "ATCC" refers to the American Tissue Culture Collection depository located in Rockville, Md. The "ATCC No." is the accession number to cultures on deposit at the ATCC.

Environmental insults capable of being detected by the detector organism of the present invention include a variety of organic and inorganic pollutants commonly found in industrial sites, waste streams and agricultural run-off. Such compounds include but are not limited to the polyaromatic hydrocarbons (PAH), the halogenated aromatics as well as a variety of heavy metals such as lead, cadmium, copper, zinc, and cobalt. Compounds demonstrated to be detected by the method of the present invention include atrazine, benzene, copper sulfate, 2,4-dichlorophenoxyacetic acid, ethanol, methanol, 2-nitrophenol, 4-nitrophenol, pentachlorophenol, phenol, toluene, dimethylsulfoxide, lead nitrate, cadmium chloride, sodium chloride, acetate, propionate, hydrogen peroxide, puromycin, mercury chloride, 2,4-dichloroaniline, propanol, butanol, isopropanol, methylene chloride, Triton X100, acrylamide, methyl viologen, mitomycin C, menadione, ethidium bromide, serine hydroxamate and xylene. Other environmental stresses detected were low phosphate levels, poor nitrogen source, poor carbon source and irradiation with ultraviolet light.

The present invention provides a method for the detection of environmental insults at sublethal levels, incorporating a detector organism containing an expressible gene fusion between a stress inducible promoter and a structural gene resulting in expression of the lux genes.

Detector organisms may include a variety of both prokaryotic and eukaryotic organisms where bacterial cells are preferred.

The present invention provides a stress inducible promoter sensitive to the presence of an environmental insult. Stress inducible promoters from both prokaryotic and eukaryotic cells may be used however promoters from bacteria are preferred and promoters from E. coli are most preferred. Suitable stress inducible promoters may be selected from, but are not limited to the list of genes under the heading "responding genes" given in Table I, below:

TABLE I

| STIMULUS | REGULATORY GENE(S) | REGULATORY CIRCUIT | RESPONDING GENES* |
|---|---|---|---|
| Protein Damage[a] | rpoH | Heat Shock | grpE, dnaK, lon, rpoD, groESL, lysU, htpE, htpG, htpI, htpK, clpP, clpB, htpN, htpO, htpX, etc. |
| DNA Damage[b] | lexA, recA | SOS | recA, uvrA, lexA, umuDC, uvrA, uvrB, uvrC, sulA, recN, uvrD, ruv, dinA, dinB, dinD, dinF etc. |
| Oxidative Damage[c] | oxyR | Hydrogen Peroxide | katG, ahp, etc. |
| Oxidative Damage[d] | soxRS | Superoxide | micF, sodA, nfo, zwf, soi, etc. |
| Membrane Damage[e] | fadR | Fatty Acid Starvation | fabA |
| Any[f] | ? | Universal Stress | uspA |
| Stationary Phase[g] | rpoS | Resting State | xthA, katE, appA, mcc, bolA, osmB, treA, otsAB, cyxAB, glgS, dps, csg, etc. |
| Amino Acid Starvation[h] | relA, spoT | Stringent | his, ilvBN, ilvGMED, thrABC, etc. |
| Carbon Starvation[i] | cya, crp | Catabolite Activation | lac, mal, gal, ara, tna, dsd, hut, etc. |
| Phosphate Starvation[j] | phoB, phoM, phoR, phoU | P Utilization | phoA, phoBr, phoE, phoS, aphA, himA, pepN, ugpAB, psiD, psiE, psiF, psiK, psiG, psiI, psiJ, psiN, |

TABLE I-continued

| STIMULUS | REGULATORY GENE(S) | REGULATORY CIRCUIT | RESPONDING GENES* |
|---|---|---|---|
| | | | psiR, psiH, phiL, phiO, etc. |
| Nitrogen Starvation[e] | glnB, glnD, glnG, glnL | N Utilization | glnA, hut, etc. |

*Genes whose expression is increased by the corresponding stimulus and whose expression is controlled by the corresponding regulatory gene(s).
[a]Neidhardt and van Bogelen in *E. coli* and *Salmonella typhimurium*; Cellular and Molecular Biology (Neidhardt, F. C., et al. Eds., pp. 1334–1345, American Society of Microbiology, Washington, DC (1987))
[b]Walker in *E. coli* and *Salmonella typhimurium*; Cellular and Molecular Biology (Neidhardt, F. C., et al. Eds., pp. 1346–1357, American Society of Microbiology, Washington, DC (1987))
[c]Christman et al. Cell 41: 753–762 (1985); Storz et al. Science 248: 189–194 (1990); Demple, Ann. Rev. Genet. 25: 315–337 (1991)
[d]Demple, Ann. Rev. Genet. 25: 31 337 (1991)
[e]Magnuson et al. Microbiol. Rev 57: 522–542 (1993)
[f]Nystrom and Neidhardt, J. Bacteriol, 175: 2949–2956 (1993); Nystrom and Neidhardt (Mol. Microbiol. 6: 3187–3198 (1992)
[g]Kolter et al. Ann. Rev. Microbiol. 47: 855–874 (1993)
[h]Cashel and Rudd in *E. coli* and *Salmonella typhimurium*; Cellular and Molecular Biology (Neidhardt, F. C., et al. Eds., pp. 1410–1438, American Society of Microbiology, Washington, DC (1987)); Winkler in *E. coli* and *Salmonella typhimurium*; Cellular and Molecular Biology (Neidhardt, F. C., et al. Eds., pp. 395–411, American Society of Microbiology, Washington, DC (1987))
[i]Neidhardt, Ingraham and Schaecter. Physiology of the Bacterial Cell: A Molecular Approach, Sinauer Associates, Sunderland, MA (1990), pp 351–388; Magasanik and Neidhardt in *E. coli* and *Salmonella typhimurium*; Cellular and Molecular Biology (Neidhardt, F. C., et al. Eds., pp. 1318–1325, American Society of Microbiology, Washington, DC (1987))
[j]Wanner in *E. coli* and *Salmonella typhimurium*; Cellular and Molecular Biology (Neidhardt, F. C., et al. Eds., *E. coli* and *Salmonella typhimurium*; Cellular and Molecular Biology (Neidhardt, F. C., et al. Eds., pp. 1326–1333, American Society of Microbiology, Washington, DC (1987))
[k]Rietzer and Magasanik in *E. coli* and *Salmonella typhimurium*; Cellular and Molecular Biology (Neidhardt, F. C., et al. Eds., pp. 1302–1320, American Society of Microbiology, Washington, DC (1987)); Neidhardt, Ingraham and Schaecter. Physiology of the Bacterial Cell: A Molecular Approach, Sinauer Associates, Sunderland, MA (1990), pp 351–388

Table I indicates the relationship of responding gene(s) with a particular regulatory gene(s) and a regulatory circuit and the associated cellular stress response triggered by a particular stimulus.

Although the majority of the stress genes listed above in Table I are known to be positively regulated, the SOS response, produced as a result of DNA damage, represents a negatively regulated circuit. For definition of positive and negative control mechanisms see Beckwith in *E. coli* and *Salmonella typhimurium*; Cellular and Molecular Biology (Neidhardt, F. C. et al. Eds., pp. 1439–1443, American Society of Microbiology, Washington, D.C. (1987)).

The SOS response to DNA damage is well understood in *E. coli*. The product of the lexA gene (the LexA repressor) binds to operator elements controlling the expression of at least 17 chromosomal genes (Walker in *E. coli* and *Salmonella typhimurium*; Cellular and Molecular Biology (Neidhardt, F. C. et al. Eds., pp. 1346–1357, American Society of Microbiology, Washington, D.C. (1987)). Upon DNA damage or interference with DNA replication, an unknown SOS-inducing signal is produced. This signal interacts with the recA gene product converting it into a form that increases the rate of proteolysis of a limited number of repressor molecules (Little, *J. Bacteriol*, 175:4943–4950). These repressor molecules are the products of the chromosomal lexA gene and repressors encoded by and expressed from ultraviolet light-inducible phage genomes in the lysogenic state. SOS promoters are released from repression by RecA protein-mediated proteolysis of the LexA repressor.

Among the SOS responsive promoters are recA and uvrA. It was seen that the recA promoter-lux fusion on a multicopy plasmid produced bioluminescence and resulted in a transformed host cell increasing bioluminescence in response to DNA damage. Although the precise mechanism of this result is not known it is clear that the invention, is not limited to the study of positively regulated global regulatory circuits because (1) some negatively regulated circuits will operate with promoters of responding genes in the multicopy state and (2) several means to place negatively controlled promoters in a single copy state exist [e.g., Oden et al., *Gene* 96:29–36 (1990); Symons et al., *Gene* 53:85–96 (1987); Winans et al., *J. Bacteriol*, 161:1219–1221 (1985); Arps and Winklet, *J. Bacteriol*, 169:1061–1070 (1987); Jasin and Schimmel, *J. Bacterioi*, 159:783–786 (1984)].

The invention also provides a transformation vector containing a stress inducible promoter-lux gene fusion, capable of transforming a bacterial host cell for the expression of the Lux proteins. A variety of transformation vectors may be used, however, those capable of transforming *E. coli* are preferred. pGrpELux.3, pGrpELux.5, pRY001, pRY002, and pRY006 are five specific examples of suitable transformation vectors whose construction is given in detail in the following text. These vectors represent only a sample of the total number of vectors created for the purpose of introducing stress promoter-lux reporter fusions into host cells. However, it will be readily apparent to one of skill in the art of molecular biology that the methods and materials used in their construction are representative of all other vectors described. Other preferred vectors are listed in Table V of Example 10.

pGrpELux.3 and pGrpELux.5 are vectors containing the grpE promoter while pRY001, pRY002 and pRY006 contain the dnaK promoter. pGrpELux.3, pGrpELux.5, and pRY006 were all created by the method of direct cloning while PCR protocols were employed as part of the construction method for pRY001 and pRY002. Transformation vectors such as these are common and construction of a suitable vector may be accomplished by means well known in the art. The preferred source of the lux genes is a pre-existing plasmid, containing a promoterless lux gene complex. Similarly, preferred sources of the stress inducible promoter DNA for the construction of the transformation vector are either also a pre-existing plasmid, where the stress inducible promoter DNA is flanked by convenient restriction sites, suitable for isolation by restriction enzyme digestion, or the product of a PCR reaction.

The pGrpELux.3 and pGrpELux.5, vectors are constructed from the *E. coli* stress gene grpE, and the lux gene complex. pGrpE4 is an *E. coli* vector derived from pUC18 (Pharmacia, Cat. No. 27–4949–01). pGrpE4 contains the grpE gene, including its promoter, bounded at the 5' end by an EcoRI site and at the 3' end by a BbuI site. Additionally, the grpE promoter is bounded at the 3' end by a PvuII site and an HaeIII site just downstream of the EcoRI site (FIG. 1). Digestion with EcoRI and BbuI restriction enzymes yields a 1.1 kb fragment which corresponds to the grpE gene. Further digestion with PvuII produces two fragments, one of which contains the grpE promoter. The 3' PvuII site on the grpE promoter fragment is converted to an EcoRI site via ligation to phosphorylated EcoRI linkers. Further digestion by HaeIII yields a grpE promoter fragment conveniently bounded by a 5' HaeIII site and a 3' PvuII site (FIG. 1).

The pUCD615 plasmid containing the lux gene complex is fully described by Rogowsky et al. (*J. Bacteriol*, 169 (11) pp 5101–512, (1987)). Plasmid pUCD615 is a 17.6 kb plasmid which contains the genes for kanamycin and ampicillin resistance and contains the promoterless lux gene operon (FIG. 1). pUCD615 is first digested with restriction enzymes EcoRI and SmaI, opening the plasmid, followed by ligation with the DNA fragments from the HaeIII digestion of pgrpE IV.

Typically, the products of the ligation reactions are screened by first transforming a suitable host and screening for bioluminescence. A variety of hosts may be used where hosts having high transformation frequencies are preferred. XL1Blue (Stratagene, LaJolla, Calif.) and DH5-α (GIBCO-BRL, Gaithersburg, Md.) are two such hosts. Preferred methods of bioluminescence screening involve exposing gridded cultures of transformants to a suitable X-ray film, followed by visual analysis of the developed films for evidence of exposure. Reisolation of the plasmid from the transformed host and restriction digests followed by gel electrophoresis is used to confirm the existence of the correct plasmid. The plasmids pGrpELux.3 and pGrpELux.5, isolated from two different transformed colonies, are indistinguishable on the basis of restriction enzyme analysis. Under some experimental conditions cells transformed with pGrpELux.5 exhibited higher baseline bioluminescence than those transformed with pGrpELux.3 and hence pGrpELux.5 is preferred for the detection of many environmental insults.

The present invention further provides a transformed host cell capable of increased luminescence in the presence of an environmental insult. Many suitable hosts are available where E. coli is preferred and the E. coli strain RFM443 is most preferred. RFM443 is derived from W3102 which is fully described by B. Bachmann, in *E. coli and Salmonella typhimurium: Cellular and Molecular Biology* (Niedhardt et al. Eds., pp 1190–1220, American Society of Microbiology, Washington, D.C. (1987)). Transformation of RFM443 by pGrpELux.3 gives the new strain TV1060 which has been deposited with the ATCC under the terms of the Budapest Treaty. Transformation of RFM443 by pGrpELux.5 gives the new strain TV1061. The baseline of bioluminescence from strain TV1061 is greater than that from strain TV1060. E. coli TV1060 has been assigned ATCC No. 69142, and TV1061 has been assigned ATCC No. 69315.

Figure 2:
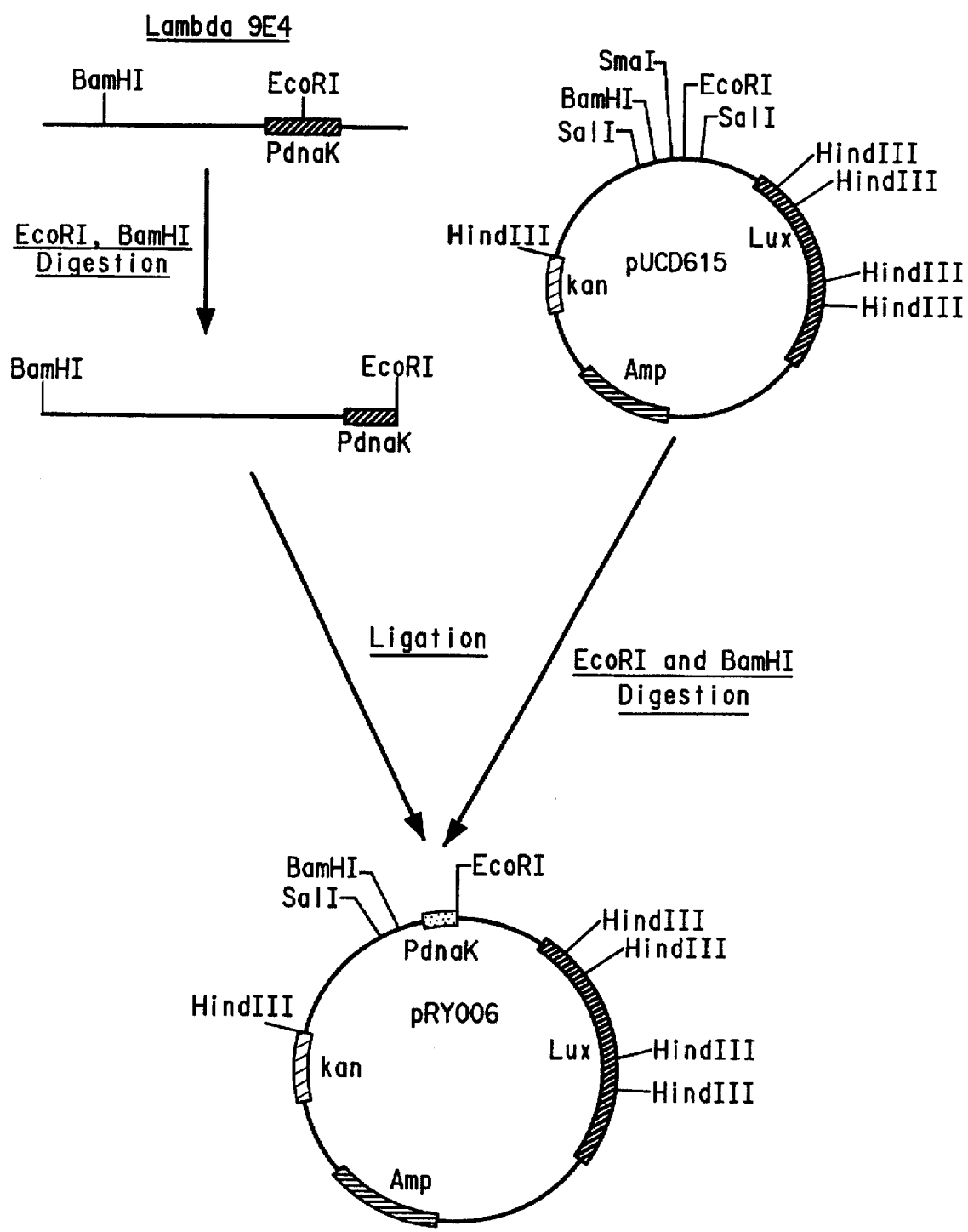
FIG. 2 is an illustration of the construction of plasmid pRY006.

The construction of the plasmid pRY006 containing the dnaK promoter followed a similar protocol to that of pGrpELux.3. DNA encoding the dnaK promoter was obtained from the Lambda phage 9E4 by digestion with the restriction enzymes EcoRI and BamHI. 9E4 is fully described by Kohara et al (Cell 50, 495–508, 1987) herein incorporated by reference. Restriction enzyme digestion produced a 3.7 kb DNA fragment encompassing the dnaK promoter region bounded on the 5' end by a BamHI site and on the 3' end by and EcoRI site. As in the construction of pGrpELux.3, the source of the lux gene complex is pUCD615. pUCD615 was first digested with BamHI and EcoRI restriction enzymes followed by ligation with the dnaK promoter fragments to produce the plasmid pRY006 (FIG. 2).

Construction of pRY001 and pRY002 is similar to that of pRY006 except that PCR protocols were used to amplify the DNA encoding the dnaK promoter from 9E4. Briefly, PCR amplification of the dnaK promoter from 9E4 was accomplished using the dnaK promoter sequence as described by Cowing et al, PNAS 82, 2679–2683, 1985 herein incorporated by reference.

Amplification was carried out as described by the manufacturer (Geneamp PCR Reagent Kit, Perkin-Elmer Cetus, Norwalk, Conn.), herein incorporated by reference. The amplified product corresponding to the dnaK promoter region contained convenient BamHI and EcoRI sites determined by the construction of the amplification primers. The dnaK promoter region was ligated to pUCD615, previously digested with restriction enzymes BamHI and EcoRI.

Ligated DNA was used to transform E. coli strain DH5α and the resulting transformants were screened for bioluminescence by exposure to X-ray film, and by restriction digests followed by analysis on agarose gels. The strain DH5-α was chosen for this initial screening due to its high transformation frequency. Two independent colonies were chosen. The two plasmids isolated from these transformants, pRY001 and pRY002, although isolated from independent colonies, are indistinguishable on the basis of restriction enzyme analysis and for the purposes of the present invention are considered identical. Under some experimental conditions cells transformed with pRY002 exhibited higher bioluminescence in response to environmental insults than those transformed with pRY001 and hence pRY002 is preferred for detection. pRY001, pRY002 and pRY006 were then used to transform RFM443 to create E. coli stain WM1021, WM1202 and WM1026 respectively. E. coli WM1021, WM1202 and WM1026 have been deposited with the ATCC under the terms of the Budapest Treaty. E. coli WM1021 has been assigned ATCC No. 69141. E. coli WM1202 has been assigned ATCC No. 69313. E. coli WM1026 has been assigned ATCC No. 69143. As mentioned above, construction of the promoters of other stress genes fused to the lux reporter was identical to the construction of pRY001 and pRY002 with the exception that the PCR primers and source of template DNA were different as dictated by the sequences of the promoters. The sequences of all of the promoters are published and are readily available through the Genbank database of nucleic acid sequences.

It is well known that hydrophobic compounds are effectively excluded by the cell envelope from entry into gram negative bacteria, such as E. coli. Recently several E. coli strains containing a mutation for tolerance to colicins (tolC⁻) have been found to have the unexpected additional property of increased permeability of host cell envelopes to various organic molecules. (Schnaitman et al. *J. Bacteriol*, 172 (9), pp 5511–5513, (1990)). Optionally, it is within the scope of the present invention to provide a transformed bacterial host containing the tolC⁻ mutation as a suitable detector organism.

In order to create a highly sensitive detector organism with enhanced cell envelope permeability to toxic organics, a tolC⁻ mutation was introduced into E. coli strain RFM443.

The E. coli transductant DE112 is isogenic to strain RFM443 except for the mutation at the tolC locus. It was constructed by phage P1 mediated generalized transduction using a lysate grown on strain CS1562 (tolC::miniTn10) (Schnaitman et al. *J. Bacteriol*, 172 (9), pp 5511–5513, (1990)) as a donor and strain RFM443 as a recipient. Resultant tetracycline resistant transductants were screened for hypersensitivity to the hydrophobic compound crystal violet.

DE112 was transformed with either pGrpELux.5 or pRY002 according to standard transformation methods as described above to create the detector organisms TV1076 (grpE lux fusion) and WM1302 (dnaK lux fusion) containing the tolC⁻ mutation. TV1076 and WM1302 have been deposited with the ATCC under the terms of the Budapest treaty and are designated ATCC No. 69314 and ATCC No. 69316 respectively.

The stress inducible promoter-lux plasmid exists in the transformed host of the present invention as an autonomously replicating plasmid; however, the routiener will recognize that it is also possible to provide a transformed host wherein the stress inducible promoter-lux plasmid is integrated into the genome of the transformed host. This may be accomplished by means known to those skilled in the art. The stress inducible promoter may drive expression of a gene product which in turn activates expression of the lux gene complex. In this case the promoter and lux gene complex might occur on different genetic elements.

As examples, any of a number of suppression mechanisms may be invoked [Hartman and Roth, Advances in Genetics, 17:1-105 (1973)]. In one, a chromosomally-integrated lux gene complex contains a nonsense mutation in either luxC, luxD, luxA, luxB or luxE and is driven by a constitutive promoter. The stress inducible promoter is fused such that it drives the expression of a nonsense suppressor gene. In the absence of stress, bioluminescence is not observed due to organisms' inability to synthesize the five requisite Lux proteins. If the organism is stressed, the suppressor gene is transcribed. Expression of the suppressor gene product allows expression of the five requisite Lux proteins and hence the organism produces light.

The method of the present invention is designed to allow for the monitoring of samples for the presence of environmental insults by using a detector organism capable of demonstrating a change in bioluminescence in response to the presence of a insult. The transformed strains TV1060, TV1061, TV1076, WM1021, WM1202, WM1302 and WM1026 are all suitable and preferred for use as detector organisms. As with the preferred vectors, these detector organisms represent only a sample of the total number of detector organisms created for the purpose of detecting environmental insults. However, it will be readily apparent to one of skill in the art of molecular biology that the methods and materials used in their construction is representative of all other vectors described. Other preferred transformed detector organisms are listed in Table V of Example 10. At optimum growth conditions a baseline level of luminescence is produced by the detector organism. Introduction of an environmental insult to the actively growing cultures will induce the stress inducible promoter which will in turn activate the lux complex, resulting in an increase in the amount of light emitted from the detector organism. The amount of light emitted is correlated to the level of the insult. For the purpose of the present invention it is most preferred if the detector organisms are actively growing in log phase just prior to exposure to sample suspected of containing an insult and at a cell density of from between about 10 Klett Units to 50 Klett Units where about 20 Klett Units is most preferred. Light emission may be monitored by a variety of methods capable of detecting photons including but not limited to visual analysis, exposure to photographic film, scintillation counting or any device incorporating a photomultiplier tube where a luminometer similar to that produced by the DynaTech Corporation is most preferred.

Figure 4:
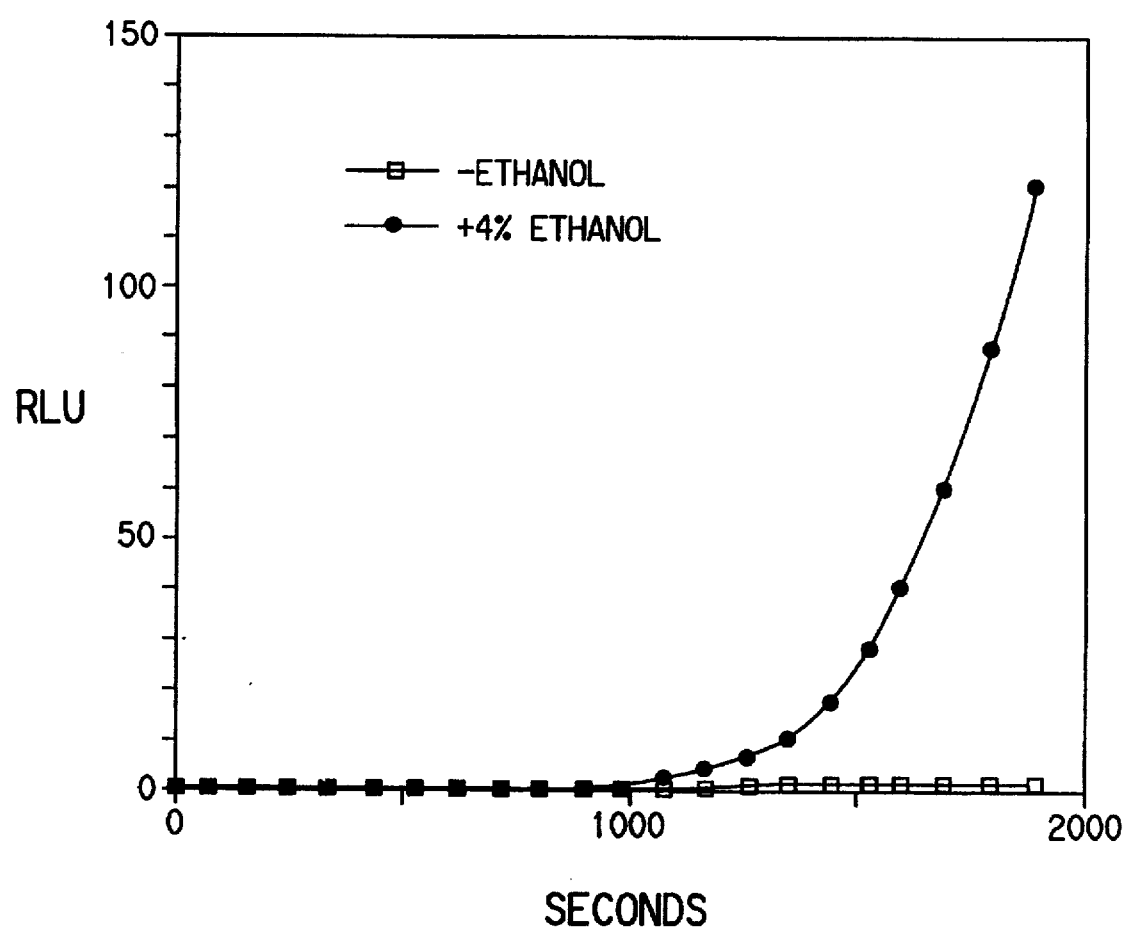
FIG. 4 is a graphic representation of the increase in luminescence by TV1060 in response to the presence of ethanol.

In one embodiment varying concentrations of ethanol were used to apply stress to detector organism. As seen in FIG. 4, a final concentration of 4% ethanol in the TV1060 cultures (containing the grpE promoter lux fushion) produced a dramatic increase in luminescence at 1000 seconds post-stress. Similarly in FIG. 5, increasing concentrations of ethanol produced a corresponding increase in luminescence from the stressed cultures. Additionally, the organic pollutants, atrazine, pentachlorophenol (PCP), phenol, 2,4-dichlorophenoxy acetic acid (2,4-D), benzene, methanol, 2-nitrophenol, 4-nitrophenol, atrazine, toluene, dimethylsulfoxide, acetate, propionate, puromycin, 2,4-dichloroanaline, propanol, butanol, isopropanol, methylene chloride, Triton X100, acrylamide, methyl viologen, serine hydroxamate, menadione, ethidium bromide, mitomycin C and xylene as well as salts of the heavy metals copper, sulfate, lead nitrate, cadmium chloride, and mercury chloride copper were detected by the present method. Also detected were high osmotic strength, ultraviolet (U.V.) light irradiation, the oxidizing agents hydrogen peroxide and growth conditions of limiting phosphate, poor nitrogen source and poor carbon source. Chemicals were either dissolved in an appropriate solvent and added to cell cultures for testing or added directly to the growth media depending on their solubility properties. Benzene, ethanol, methanol, propanol, isopropanol, butanol, methylene chloride, dimethyl sulfoxide, Triton X-100, phenol, toluene, and xylene were added directly to LB medium, whereas 2-nitrophenol, 4-nitrophenol, and atrazine were first dissolved in methanol before being diluted into LB medium. Copper sulfate, lead nitrate, cadmium chloride, mercury chloride, sodium chloride, sodium acetate, sodium propionate, hydrogen peroxide, puromycin, methyl viologen, acrylamide, menadione, ethidium bromide, serine hydroxamate, and mitomycin C were first dissolved in water before being diluted into LB medium. Pentachlorophenol (PCP), 2,4-dichlorophenoxy acetic acid, and 2,4-dichloroaniline were first dissolved in ethanol and finally diluted into LB medium for testing. In all cases, the final concentration of either ethanol or methanol, or the slight dilution of the medium with water were such that it did not induce a significant response.

Figure 7:
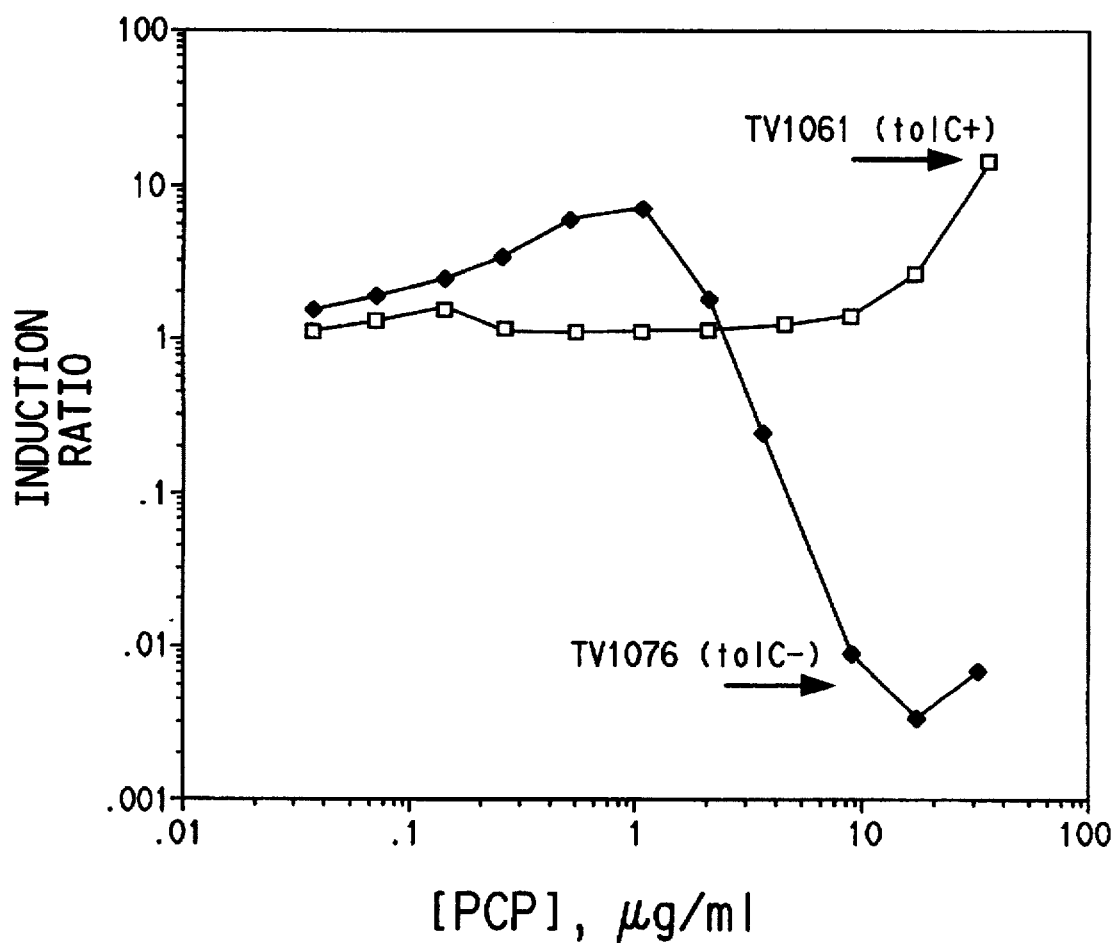
FIG. 7 is a graphic representation of the relative sensitivities of tolC$^+$ and tolC$^-$ detector cells transformed with pGrpE.Lux.5 to pentachlorophenol.

The data shown in FIG. 7 and Tables II and III demonstrate two aspects of the present detection system. First, that organic and inorganic pollutants can be detected at low concentrations by the instant method and secondly, that the sensitivity of the system can be enhanced by the use of a host detector organism containing the tolC$^-$ mutation.

FIG. 7 compares the relative sensitivities of detector organisms transformed with the GrpE.Lux.5 fusion with and without the tolC$^-$ mutation to the presence of pentachlorophenol. As can be seen by the data, the tolC$^-$ mutants exhibit significantly higher sensitivity to the presence of the PCP than the tolC$^+$ parental strain. Table III (Example 9) contains data comparing the relative sensitivities of detector organisms transformed with the pYR002 fusion with and with out the tolC$^-$ mutation to the presence of PCP, 2,4-D, phenol, atrazine, ethanol, methanol, 2-nitrophenol and copper sulfate. Similarly, it is evident that PCP and 2,4-D are preferentially detected by the tolC$^-$ mutant host. The tolC$^-$ host also appears to be more sensitive to phenol, although to a lesser extent than with PCP and 2,4-D. The tolC$^-$ mutation appears to have little effect on the sensitivity of the detector organism to non-organic contaminants such as copper sulfate which would be expected in light of the fact that the tolC$^-$ mutation is known to increase the host cell envelope permeability only to hydrophobic compounds.

Optionally, the method of the present invention may also be used to detect lethal levels of a insult by measuring the decrease in the baseline luminescence produced by the detector organism. Lethal levels of insults will interfere with either central metabolism or any lux protein function of the detector organism, which would be indicated by a decrease in light emitted from the cultures.

Figure 6A:
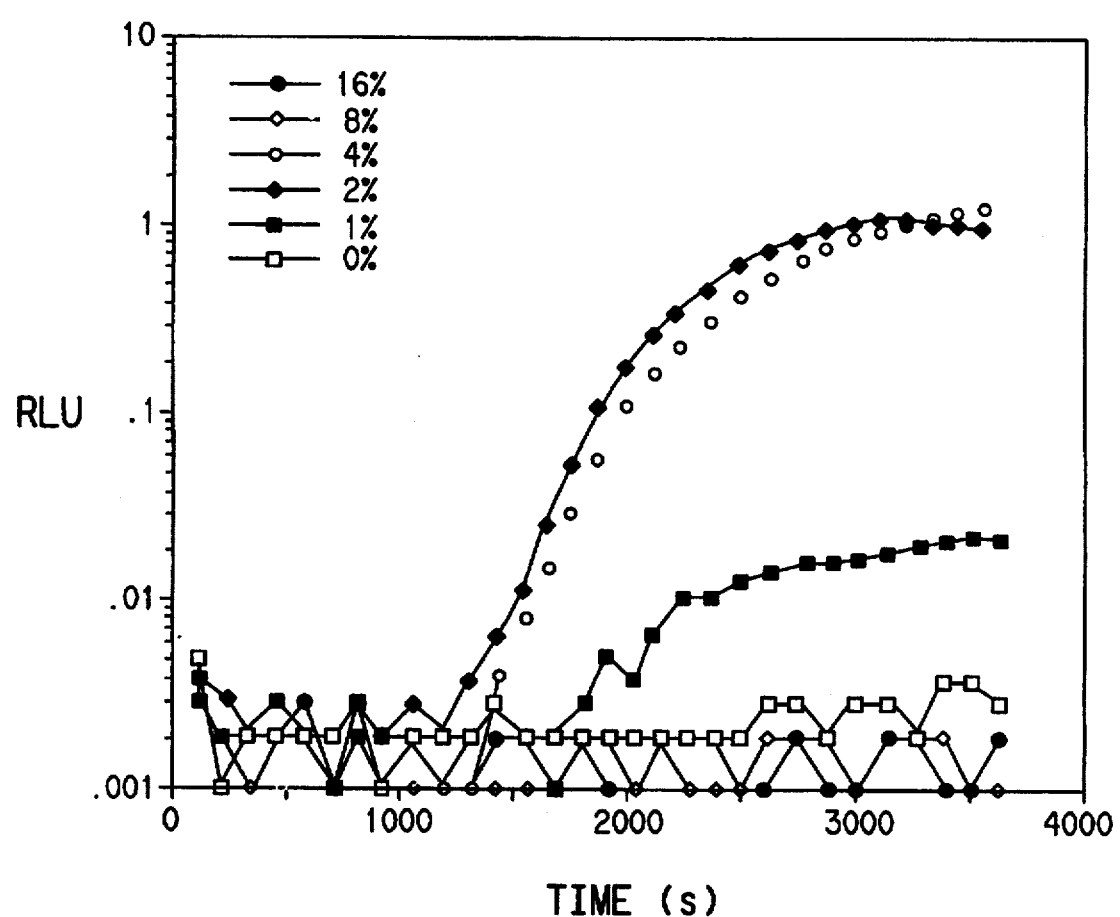
FIG. 6a is a graphic representation of the increase in luminescence by WM1021 in response to the presence of varying concentrations of ethanol.

FIGS. 6a and 6b illustrate the sensitivity of the transformants WM1021 and WM1026 (containing the dnaK promoter lux fushion) to the stress of varying concentrations of ethanol. It is interesting to note that at the sublethal concentrations of ethanol varying from 1% to 4%, light emission increased in a fashion similar to the TV1060 cultures. By contrast, lethal concentrations of ethanol in the ranges of 8% to 16% produced a decrease in light emission from the detector cultures. Likewise, higher concentrations of PCP also result in decrease of light output in strain TV1076 (FIG. 7). Thus, it is evident that the method of the present invention is capable of a bi-modular function. In one mode, detection of insults at sublethal levels are possible via the mechanism of the induction of the stress inducible promoter and the subsequent increase in light production from the detector organism. In an alternate mode, levels of insults capable of interfering with central cellular metabolism can also be detected since bioluminescence is an energy and reducing power dependant phenomenon and any interference with central metabolism will cause the baseline luminescence to decrease. Moreover, it is evident that the induction of light production from the stress promotor-lux fushions occurs at lower concentrations of specific pollutants than those concentrations required to result in a decrease of light output.

The following non-limiting Examples are meant to illustrate the invention but are not intended to limit it in any way.

MATERIALS AND METHODS

Restriction enzyme digestions, phosphorylations, ligations and transformations were done as described in Sambrook, J. et al., Molecular Cloning: A Laboratory Manual, Second Edition (1989) Cold Spring Harbor Laboratory Press. Isolation of restriction fragments from agarose gels used Qiagen columns (Qiagen, Inc.) and was performed as specified by the manufacturer. Strataclean (Stratagene, LaJolla, Calif.) and GeneClean (Bio101) were used to remove enzymes from restriction digests, as specified by the manufacturers. The meaning of abbreviations is as follows: "h" means hour(s), "min" means minute(s), "sec" means second(s), and "d" means day(s).

EXAMPLES

Example 1

Construction of Plasmids pGrpELux.3 and pGrpELux.5 and Transformation of RFM443

The outline of the scheme used to construct these plasmids is shown in FIG. 1. FIG. 1 is meant to illustrate the events of the construction, however DNA constructs are not drawn to scale.

Plasmid pGrpE4 was derived from pUC18 (Pharmacia, Cat. No. 27-4949-01) and contains the Escherichia coli stress gene, grpE, including its promoter sequences. pGrpE4 plasmid was digested with restriction enzymes EcoRI and BbuI and a 1.1 kb fragment was isolated following agarose gel electrophoresis corresponding to the grpE promoter and structural gene (FIG. 1). The grpE promoter is conveniently bounded on the 5' end by an EcoRI site and on the 3' end by a PvuII site. The isolated fragment was further digested with restriction enzyme PvuII, separating the promoter region from the structural gene (FIG. 1). An EcoRI linker fragment (Stragene, Catalog #901027) was phosphorylated and then ligated to the products of the PvuII digestion replacing the 3' PvuII site on the promoter with an EcoRI site. Further digestion with HaeIII produced a series of fragments, one of which contains the grpE promoter bounded on the 5' end by HaeIII and on the 3' end by EcoRI (FIG. 1).

Plasmid pUCD615 (J. Bacteriol, 169 (11) pp 5101–512, (1987)) is a 17.6 kb plasmid which contains the genes for kanamycin and ampicillin resistance and contains the promoterless lux gene operon with multiple cloning sites upstream of the start of lux. (FIG. 1). The pUCD615 is first digested with restriction enzymes EcoRI and SmaI, opening the plasmid, followed by ligation with the DNA fragments from the HaeIII digestion (FIG. 1).

In order to screen for active grpE-lux fusion ligated DNA was used to transform E. coli strain XL1Blue (Stratagene) by standard $CaCl_2$ transformation protocols and screened for the presence of plasmids using kanamycin resistance. Colonies were grown in gridded fashion on LB medium containing kanamycin (25 µg/mL) at 37° C., overnight and were further screened for bioluminescence to determine which transformants contained promoter sequences fused to the lux genes of pUCD615. Bioluminescent screening was done by exposing the gridded colonies to X-OMAT AR film (Kodak, Rochester, N.Y.) at ambient temperature and analyzing the developed films visually. Confirmation of transformation by the expected plasmid was further obtained by agarose gel electrophoretic analysis of plasmid DNA from cells producing light following restriction digests, for the presence and size of restriction fragments. Restriction fragments from Hind III, BamHI, and Sal I digestions confirmed the presence and orientation of the grpE promoter in plasmids pGrpELux.3 and pGrpELux.5.

Plasmids pGrpELux.3 and pGrpELux.5. were moved by transformation into E. coli host strain RFM443 to give E. coli strains TV1060 and TV1061 respectively. E. coli RFM443 was originally derived from E. coli W3102 which is fully described in by B. Bachmann, in E. coli and Salmonella typhimurium: Cellular and Molecular Biology (Neidhardt, F. C. et al. Eds., pp 1190–1220, American Society of Microbiology, Washington, D.C. (1987))

Example 2

Construction of Plasmid pRY006 and Transformation of RFM443

The outline of the scheme used to construct pRY006 is shown in FIG. 2. FIG. 2 is meant to illustrate the events of the construction, however DNA constructs are not drawn to scale.

DNA containing the dnaK promoter was obtained from Lambda phage 9E4 (Kohara, Y. et al; Cell 50, 495–508, 1987) using a Magic Lambda Prep, following the manufacturers suggested protocol (Promega Corp., Madison, Wis.). Phage DNA was digested with restriction enzymes BamHI and EcoRI. Several DNA fragments were liberated by this treatment including a 3.7 Kb BamHI-EcoRI restriction fragment encompassing the dnaK promoter region as described by Cowing et al (PNAS 82, 2679–2683, 1985), and approximately 3.0 kb of DNA 5' to this region, and 700 bp 3' of the promoter region encoding the amino terminus of the DnaK protein. Digested DNA was ligated to pUCD615 which had been digested previously with restriction enzymes BamHI and EcoRI (FIG. 2). The resulting plasmid constructs were used to transform E. coli strain DH5-α (GIBCO-BRL, Gaithersburg, Md., Catalog No. 82635a), and transformed bacteria were plated on LB medium containing 50 µg/mL kanamycin, overnight at 37° C. Resulting colonies were initially screened for bioluminescence by exposure to X-OMAT AR film as described in Example 1. Presence of the desired plasmid construction was confirmed by restriction enzyme analysis of plasmid DNA from transformed bacteria. Digestion with restriction enzymes BamHI and EcoRI yielded a 3.7 Kb restriction fragment following agarose gel electrophoresis, confirming the presence of the desired construction. This plasmid was designated pRY006. pRY006 was introduced into *E. coli* strain RFM443 by transformation creating strain WM1026.

Example 3

Construction of Plasmid pRY001 and pYR002 and Transformation of RFM443

Figure 3:
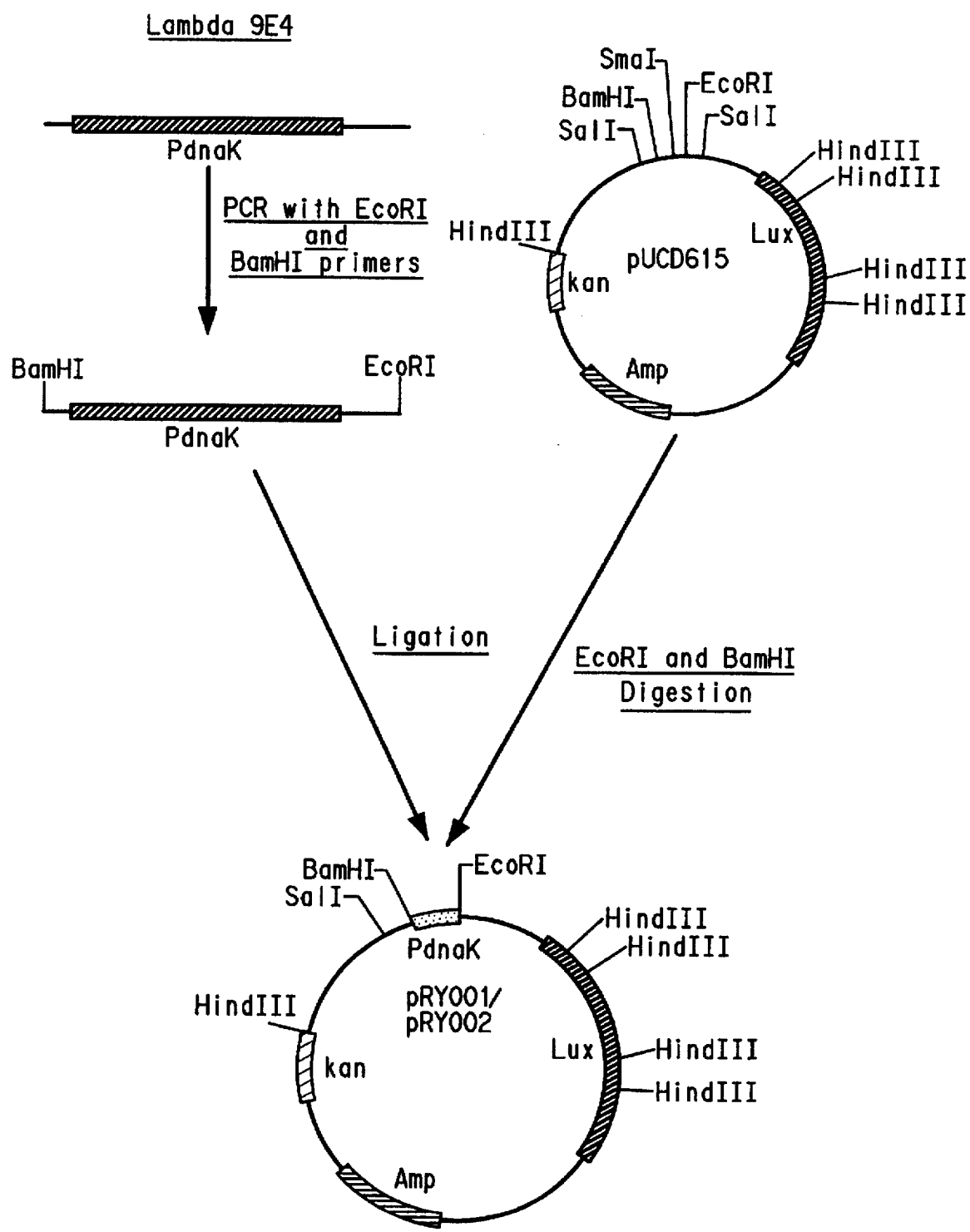
FIG. 3 is an illustration of the construction of plasmid pRY001 and pYR002.

The outline of the scheme used to construct this plasmid is shown in FIG. 3. FIG. 3 is meant to illustrate the events of the construction; however DNA constructs are not drawn to scale.

DNA containing the dnaK promoter (described by Cowing et al., PNAS 82, 2679–2683, 1985) was obtained from Lambda phage 9E4 (Kohara, Y. et al., *Cell* 50, 495–508, 1987) using a Magic Lambda Prep (Promega Corp., Madison, WI), following the protocol as described by the manufacturer. PCR amplification of the dnaK promoter region was accomplished using the following amplification primers:

Upper: 5'-GTTAGCGGATCCAAAAGCACAAAAAAT-3' (SEQ ID NO. 1)

Lower: 5'-AGCAGTGAATTCCATCTAAACGTCTCCA-3' (SEQ ID NO. 2)

DNA amplification was carried out as described by the manufacturer (GeneAmp PCR Reagent Kit, Perkin-Elmer Cetus, Norwalk, Conn.). Reagent concentrations were:

1×Buffer 200 uM dATP 200 uM dCTP 200 uM dGTP 200 uM dTTP 2.5 units Amplitaq Polymerase (Perkin-Elmer Cetus)

100 pM Upper Primer 100 pM Lower Primer 1 ng 9E4 phage DNA Template $dH_2O$ to 100 µL The reaction was performed using a Perkin-Elmer Cetus GeneAmp PCR System 9600 thermal cycler programmed as follows:

Melting: 94° C. for 10 sec

Annealing: 50° C. for 10 sec

Extension: 72° C. for 15 sec

Cycles: 30

The amplified product which results is 207 base pairs in length, and contains the entire 182 bp segment encoding the dnaK promoter region as deposited in GeneBank (Accession 10420; Locus ECODNAK), as well as short 5' and 3' flanking sequences. PCR-amplified DNA was digested with restriction enzymes BamHI and EcoRI, and ligated to pUCD615 previously digested with restriction enzymes BamHI and EcoRI (FIG. 3). The resulting plasmid constructs were introduced into the *E. coli* strain DH5-α (GIBCO-BRL, Gaithersburg, Md., Cat. No. 82635a) by standard transformation protocols, and bacteria were plated on LB medium containing 50 µg/mL kanamycin and grown overnight at 37° C. Resulting colonies were initially screened for bioluminescence by exposure to X-ray film as described in Example 1. Two colonies were picked for transformation analysis and the presence of the desired plasmid construction was confirmed by restriction enzyme analysis of plasmid DNA from transformed bacteria.

Appearance of a 193 bp BamHI-EcoRI restriction fragment following agarose gel electrophoresis confirmed the presence of the desired construction. These plasmids were designated pRY001 and pRY002. Although pRY001 and pRY002 represent different transformation colonies they are indistinguishable on the basis of restriction enzyme mapping and for the purposes of the present invention are considered identical. pRY001 and pRY002 were introduced into *E. coli* strain RFM443 by transformation creating strains WM1021 and WM1202, respectively.

Example 4

Stress Induction of Bioluminescence at 4% Ethanol

Strain TV1060 was grown at 37° C. in LB medium containing kanamycin (25 µg/mL) until it reached Klett 56 (measured on a Klett-Summerson colorimeter with a #66 red filter) at which time it was diluted 1:11 into the same medium at ambient temperature and allowed to grow for 3 h at ambient temperature until reaching a density of 20 Klett Units. 100 µL of cells were placed into the wells of a microtiter plate followed by the addition of either 10 µL 40% ethanol (experimental, final concentration 4% ethanol) or 10 µL of distilled water (control). The plate was immediately placed into a luminometer (Luminoskan, Finland) and bioluminescence was measured as RLU vs. time. As can be seen in FIG. 4, light emission from the transformed TV1060 cultures stressed with 4% ethanol increased dramatically 1000 sec post-stress reaching a maximum level of 130 RLU. Addition of the distilled water to the control cultures produced no variation in the baseline luminescence (FIG. 4).

Example 5

Stress Induction of Bioluminescence at Varying Concreations of Ethanol

Figure 5:
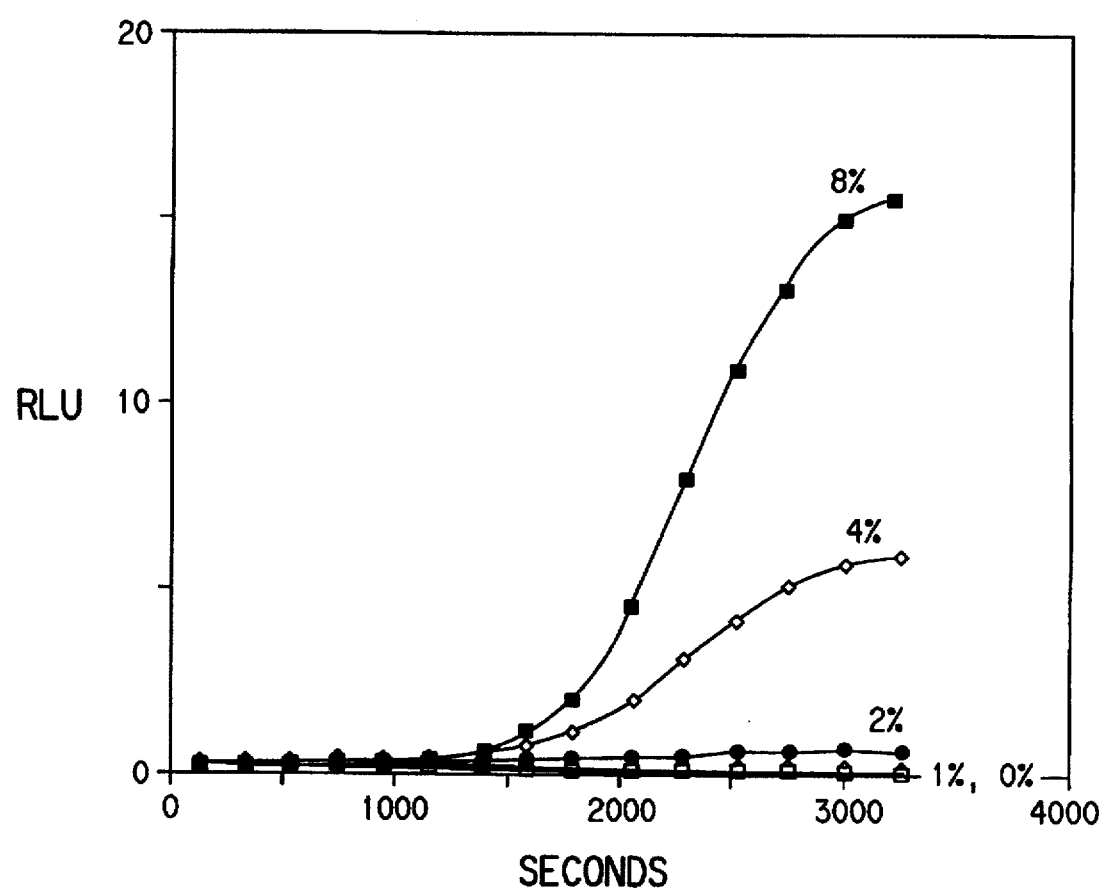
FIG. 5 is a graphic representation of the increase in luminescence by TV1060 in response to the presence of increasing concentrations of ethanol.

Strain TV1060 was grown overnight in LB medium containing kanamycin (25 µg/mL) and then diluted 1:100 in the same medium and grown at room temperature until reaching a Klett of 20. 100 µL of cells were placed into the wells of a microtiter plate containing 100 µL of either 2%, 4%, 8% or 16% (giving final concentrations of 1%, 2%, 4%, and 8% respectively of ethanol, experimental) or 100 gL of the same medium (control). The plate was immediately placed into a luminometer, model ML3000 (Dynatech Laboratories, Chantilly, Va.) and bioluminescence was measured as RLU vs. time. As can be seen in FIG. 5, light emission from the transformed TV1060 cultures stressed with ethanol demonstrated an increase in luminescence corresponding to increasing concentrations of ethanol. As in Example 4, increases in luminescence were observed after 1000 sec post-stress. Control cultures produced no variation in the baseline luminescence (FIG. 5). Maximum light emission was obtained with 8% ethanol at 3000 sec post-stress showing a 263 fold increase in light production over the control. Lower levels of ethanol stress produced correspondingly lower levels of light output where 4%, 2%, and 1% ethanol concentrations gave 96, 13.5 and 3.9 fold increases in light emission over the controls, respectively.

Example 6

Stress Induction of Bioluminescence in Strains WM1021 and WM1026

Strains WM1021 and WM1026 were grown at 37° C. for approximately 18 h in LB medium containing kanamycin (50 µg/mL). Cultures were then diluted 1:50 into the fresh media, and grown at ambient temperature for approximately 3 h. When cells reached a density of Klett Units of 20, 80 µL of the cell suspension was placed into the wells of a microtiter plate containing 20 µL of ethanol at various concentrations, and the plate was immediately placed into a Dynatech Model ML3000 luminometer. Ethanol was present at final concentrations of 16%, 8%, 4%, 2%, and 1%, and a deionized water control was included. The luminometer was previously programed to measure luminescence at 2 min intervals. FIGS. 6a and 6b present the resulting luminescence data produced in response to varying concentrations of ethanol by strains WM1021 and WM1026, respectively. As shown in FIG. 6a luminescence increases sharply 1000 sec post-stress in those cultures receiving the sublethal concentrations of 1%, 2% and 4% ethanol. At the higher, lethal concentrations of ethanol of 8% and 16%, luminescence was seen to decline below baseline values, suggesting cell death. FIG. 6b shows similar results using the host cell WM1026. Thus, light is increased in response to sublethal levels of ethanol whereas light output is diminished at higher, lethal levels. This example demonstrates the ability of the invention to detect the presence of both sublethal and lethal levels of an insult.

Example 7

Comparison of Stress Induction of Bioluminescence by Pentachlorophenol in tolC$^+$ and tolC$^-$ Strains Transformed with pGrpE.Lux.5

In order to provide an *E. coli* detector organism with enhanced permeability to organic compounds the tolC$^-$ mutant DE112 was constructed from RFM443. The *E. coli* strain DE112 is isogenic to strain RFM443 except for the mutation at the tolC locus. It was constructed by phage P1 mediated transduction using a lysate grown on strain CS1562 (tolC::miniTn10) as a donor and strain RFM443 as a recipient. CS1562 (tolC::miniTnlO) is fully described in Austin et al., *J. Bacteriol.* 172, 5312, (1990) and the transduction procedure is described in Miller, J. H., *Experiments in Molecular Genetics*, (1972) Cold Spring Harbor Laboratory, Cold Spring Harbor, N.Y., pp 201–205. RFM443 was originally derived from W3102 which is fully described in by B. Bachmann, in *E. coli and Salmonella typhimurium: Cellular and Molecular Biology* (Niedhardt et al. Eds., pp 1190–1220, American Society of Microbiology, Washington D.C., (1987)). Resultant tetracycline resistant recombinants were screened for hypersensitivity to the hydrophobic compound crystal violet.

DE112 and RFM443 are isogenic except at the tolC locus. Both strains were transformed with the plasmid pGrpELux.5 as described in Example 1, and designated TV1076 (tolC::miniTn10) and TV1061 (tolC$^+$) respectively.

Both strains were grown overnight at 25° C. in LB medium containing Kanamycin at 50 µg/mL. The overnight cultures were diluted 1:50 into fresh LB medium containing Kanamycin (50 µg/mL) and were incubated with shaking at 25° C. for 4 h. Cell density was determined on a Klett-Summerson colorimeter. When both strains reached readings of between 25 and 29 Klett Units the cells were used for testing.

Cells (50 µL) from each culture were added to LB medium containing Kanamycin (50 µg/mL) and various concentrations of pentachlorophenol (PCP) in the wells of a microtiter plate such that the final volume in each well was 100 µL.

A 100 mg/mL stock solution of PCP in ethanol was used to make a 75 µg/mL solution of PCP in LB medium containing Kanamycin (50 µg/mL). This solution (50 µL) was placed in wells of a microtiter plate and serial two-fold dilutions were made of from these. When the equal volume of cells was added, the highest ethanol concentration was 0.037%, a concentration known not to induce a significant response from these cells.

Light readings were taken at periodic intervals, in a Dynatech ML3000 microtiter plate luminometer at 25° C., and the data is shown in the graph of FIG. 7 plotted as concentration of PCP as a function of induction ratio. The induction ratio is defined as the light output (RLU) in the presence of PCP divided by the light output (RLU) in the absence of PCP.

FIG. 7 shows the induction ratio at 60 min after the addition vs. the dose of PCP. At low doses, no induction of light output (ratio=1) from the tolC$^+$ strain, TV1061, was seen. However, at these lower doses the tolC$^-$ strain, TV1076, showed significant increase of light output. Also, at higher doses, the induction in the tolC$^+$ strain is observed, and a toxic effect of the PCP (loss of light output) is observed in the tolC$^-$ strain. Thus, the tolC$^-$ strain is useful for detecting lower concentration of this compound than can be detected in the tolC$^+$ strain. Likely, other hydrophobic compounds will also be more readily detected by the combination of this host strain with the plasmids containing grpE:: lux fusions Example 8

Stress Induction of Bioluminescence by Organic and Inorganic Pollutants in tolC$^+$ and tolC$^-$ Strains Transformed with PGrpE.Lux.5

TV1061 and TV1076 were engineered as described above. Both strains were grown overnight at 25° C. in LB medium containing Kanamycin at 50 µg/mL. The cover night cultures were diluted between 40 and 100-fold into fresh LB medium containing Kanamycin (50 µg/mL) and were incubated with shaking at 25° C. Cell density was determined on a Klett-Summerson colorimeter. When both strains gave readings of between 15 and 30 Klett Units, cells were used for testing.

Cells (50 BL) from each culture were added to LB medium containing Kanamycin (50 µg/mL) and various concentrations of benzene, ethanol, methanol, 2-nitrophenol, 4-nitrophenol, PCP, phenol, toluene, and xylene in the wells of a microtiter plate such that the final volume in each well was 100 BL. Control wells contained appropriate volumes of solvents used to dissolve the test compounds.

Benzene, ethanol, methanol, propanol, isopropanol, butanol, methylene chloride, dimethyl sulfoxide, Triton X-100, phenol, toluene, and xylene were added directly to LB medium containing kanamycin (50 µg/mL). Stock solutions in methanol of 2-nitrophenol (136 mg/mL) and of 4-nitrophenol (112 mg/mL) were diluted into LB medium containing kanamycin (50 µg/mL) to concentrations tested. The final concentration of methanol was such that it did not induce a significant response form these cells. A stock solution in ethanol of PCP (100 mg/mL) was diluted into LB medium containing kanamycin (50 Bg/mL) to the concentration tested. The final concentration of ethanol was such that it did not induce a significant response from these cells. Stock solutions in water of copper sulfate (250 mM), lead nitrate (100 mM), mercury chloride (100 mM), sodium chloride (20%), sodium acetate (2M), sodium propionate (2M), hydrogen peroxide (30%), puromycin (10 mg/mL), methyl viologen (200 mg/mL), and acrylamide (1M) were diluted into LB medium containing kanamycin (50 μg/mL) to the concentrations tested. A stock solution in water of cadmium chloride (100 mM) was diluted into LB medium lacking kanamycin to the concentrations tested.

Light readings were taken at periodic intervals over a two h period and the data is shown in Table II. All luminescence readings were measured in a Dynatech ML3000 microtiter plate luminometer at 25° C.

Data in Table II represent readings taken 1 h post exposure to the test compounds and are expressed as the concentration of test compound that gives the maximum luminescence. Data are also given showing the fold increase in induced luminescence over the baseline luminescence.

pRY002 by standard methods as described in Example 3, and designated WM1302 (tolC::miniTn10) and WM1202 (tolC$^+$) respectively.

Both strains were grown overnight at 25° C. in LB medium containing Kanamycin at 50 μg/mL. The overnight cultures were diluted 1:100 into fresh LB medium containing Kanamycin (50 μg/mL) and were incubated with shaking at 25° C. for 4 h. Cell density was determined on a Klett-Summerson colorimeter. When both strains gave readings of 28 Klett Units, cells were used for testing.

Cells (50 μL) from each culture were added to wells of a microtiter plate containing LB medium containing Kanamycin (50 μg/mL) and various concentrations of PCP, 2,4-dichlorophenoxyacetic acid (2,4-D), phenol, ethanol, methanol, 2-nitrophenol, atrazine and copper sulfate such that the final volume in each well was 100 μL. Control wells

TABLE II

Induction of Light Production from Plasmid pGrpELux.5 by Chemicals

| | TV1061 (tolC$^+$) | | TV1076 (tolC$^-$) | |
|---|---|---|---|---|
| Chemical | Conc. for Max Induction | Fold Increase | Conc. for Max Induction | Fold Increase |
| Benzene | 10 mg/mL* | 1.8 | 10 mg/mL* | 2 |
| Ethanol | 2% (v/v) | 182 | 2% (v/v) | 140 |
| Methanol | 4% (v/v) | 40 | 4% (v/v) | 17 |
| 2-nitrophenol | 113 μg/mL | 2.5 | 113 μg/mL | 2.5 |
| 4-nitrophenol | 37 μg/mL | 4.7 | 37 μg/mL | 3 |
| Pentachlorophenol | 37.5 μg/mL* | 15.3 | 1.17 μg/mL | 6.7 |
| Phenol | 460 μg/mL | 12 | 460 μg/mL | 11.1 |
| Toluene | 10 mg/mL* | 2.7 | 10 mg/mL* | 3.2 |
| Xylene | 3.3 mg/mL | 1.7 | 3.3 mg/mL | 1.4 |
| 2,4-Dichlorophenoxy acetic acid | 133 μg/mL | 13.1 | 133 μg/mL | 9.3 |
| Copper Sulfate | 1000 μg/mL | 6.3 | 1000 μg/mL | 5.5 |
| Dimethyl Sulfoxide | 1% (v/v)* | 2.9 | 1% (v/v) | 2.6 |
| Lead Nitrate | 800 μM* | 2.4 | | |
| Sodium Chloride | 2% (w/v)* | 9.2 | | |
| Cadmium Chloride | 333 μM | 9.7 | | |
| Sodium Acetate | 50 mM | 14 | | |
| Sodium Propionate | 100 mM* | 76 | | |
| Hydrogen Peroxide | 0.0093% (w/v) | 54.5 | 0.0046% (w/v) | 6.1 |
| Puromycin | 50 μg/mL | 1.6 | Only inhibition detected | |
| Mercury Chloride | 0.39 μM | 1.4 | 0.39 μM | 1.6 |
| 2,4-dichloroaniline | 100 μg/mL* | 49.4 | 100 μg/mL* | 49.4 |
| Propanol | 2% (v/v) | 84.8 | | |
| Isopropanol | 2% (v/v) | 124 | | |
| Butanol | 0.5% (v/v) | 27.7 | | |
| Methylene Chloride | 4% (v/v) | 11.4 | | |
| Triton X-100 | 1% (v/v)* | 1.2 | | |
| Methyl Viologen | 50 μg/mL | 2 | | |
| Acrylamide | 50 mM* | 1.9 | | |

*Maximum concentration tested

It is evident from the data in Table II that a wide variety of chemical compounds and environmental conditions will induce bioluminescence from *E. coli* strains containing the plasmid pGrpELux.5. Hence, it may be concluded that detector organisms containing the tolC$^-$ mutation represent a preferred host for some environmental insults.

Example 9

Stress Induction of Bioluminescence by Organic and Inorganic Pollutants in tolC$^+$ and tolC$^-$ Strains Transformed with pRY002

DE112 (tolC::miniTn10) was engineerd as described in Example 7, and the source of RFM443 has beeen previously discussed. Both strains were transformed with the plasmid contained appropriate volumes of solvents used to dissolve the test compounds.

Chemicals were prepared for testing essentially as described in Example 8. Copper sulfate was added directly to the culture medium and atrazine was first dissolved in methanol before additions to cell cultures. With the exception of atrazine, all solvents were added at levels below those needed to see a stress response in the system. The level of methanol present in the atrazine sample induced a low but detectable response; data in Table III is the net response detected above the response obtained with an equivalent amount of methanol alone.

Light readings were taken at periodic intervals over a two h period and the data is shown in Table III. All luminescence readings were measured in a Dynatech ML3000 microtiter plate luminometer at 25° C.

Data in Table III represent readings taken 1 h post exposure to the test compounds and are expressed as the concentration of test compound that gives the maximum luminescence. Data are also given showing the fold increase in induced luminescence over the baseline bioluminescence.

TABLE III

Induction of Bioluminescence from Cells
Transformed with Plasmid pRY002 by Chemicals

|  | WM1202 (tolC+) | | WM1302 (tolC−) | |
| --- | --- | --- | --- | --- |
| Chemical | Conc. for Max Ind.** | Fold Incr.*** | Conc. for Max. Ind. | Fold Incr. |
| Atrazine | 135 µg/mL* | 2.2 | no ind. | — |
| Copper Sulfate | 3.3 mM* | 9 | 3.3 mM* | 8.4 |
| Ethanol | 4% (v/v) | 1264 | 4% (v/v) | 1525 |
| 2,4-D | 400 µg/mL* | 42 | 100 µg/mL | 140 |
| Methanol | 5% (v/v) | 3.7 | 5% (v/v) | 3.9 |
| 2-nitrophenol | 340 µg/mL* | 7.6 | 340 µg/mL* | 9.3 |
| PCP | 37.5 µg/mL* | 106 | 1.2 µg/mL | 45 |
| Phenol | 1.4 mg/mL | 6 | 1.4 mg/mL | 72 |

*Maximum concentration tested
**"Conc. for Max. Ind." means concentration for maximum induction
***"Fold Incr." means the fold increase over baseline bioluminescence It is evident from the data in Table III that several classes of chemical compounds will induce bioluminescence from E. coli strains containing the plasmid pRY002. Both the tolC− and tolC+ hosts demonstrated similar sensitivities to less hydrophobic compounds. It may be concluded that detector organisms containing the tolC− mutation represent a preferred host for some environmental insults.

Example 10

Construction of Promoters lon, recA, uvrA, katG, micF, uspA, xthA, his, lac, phoA, glnA Fused to the lux operon The scheme to construct additional plasmids is identical to the construction of pRY001 and pRY002 as illustrated in FIG. 3 and described in Example 3, with the exception that different primers and templates were used for the PCR reactions, and that 40 cycles were used in PCR reactions. The primers and templates used are listed below in Table IV.

TABLE IV

| Target Promoter[a] | Upper Primer (5' to 3')[b] | Lower Primer (5' to 3')[c] | Template[d] | Product Size (bp)[e] |
| --- | --- | --- | --- | --- |
| lon | ACTTAAGGATCCAAGCGATGGCGCGTAAAA SEQ ID NO:3 | AGCAGCGAATTCATCGCCGCTTCCAGACAA SEQ ID NO:4 | 148 | 534 |
| recA | ACTTAAGGATCCAGAGAAGCCTGTCGGCAC SEQ ID NO:5 | AGCTTTGAATTCCGCTTCTGTTTGTTTT SEQ ID NO:6 | C | 279 |
| uvrA | ACTTTTGGATCCGTGTAAACGCGCGATTG SEQ ID NO:7 | AGCAGCGAATTCTTCCCGGATTAAACGCTT SEQ ID NO:8 | 637, 638 | 225 |
| katG | ACTTAAGGATCCCGAAATGAGGGCGGGAAA SEQ ID NO:9 | AGCAGCGAATTCGAACGTTGCTGACCACGA SEQ ID NO:10 | 538 | 654 |
| micF | ACTTAAGGATCCCCCCAAAAATGCAGAATA SEQ ID NO:11 | AGCAGCGAATTCGGGCATCCGGTTGAAATAG SEQ ID NO:12 | 373 | 331 |
| fabA | ACTTAAGGATCCGCCATTACGTTGGCTGAA SEQ ID NO:13 | AGCAGCGAATTCCCACCCGTTTCGGTCATT SEQ ID NO:14 | 222 | 260 |
| uspA | ACTTAAGGATCCCTCCCGATACGCTGCCA SEQ ID NO:15 | AGCAGCGAATTCGGCGATGAGAATGTGTTTAT SEQ ID NO:16 | 608 | 381 |
| xthA | ACTTAAGGATCCAATTACTGCGCCATTCTG SEQ ID NO:17 | ACATCGGAATTCTCATAGTCGCTGCCATTT SEQ ID NO:18 | C | 181 |
| his | ACTTAAGGATCCCTAATTGTACGCATGTCA SEQ ID NO:19 | AGCAGCGAATTCAAAGTCTCTGTGAATGTT SEQ ID NO:20 | 350 | 301 |
| phoA | ACTTAAGGATCCAGATTATCGTCACTGCAA SEQ ID NO:21 | AGCAGCGAATTCGGCCAATCAGCAAAATAA SEQ ID NO:22 | 141, 142 | 501 |
| glnA | ACTTTCGGATCCTTGGTGCAACATTCACAT SEQ ID NO:23 | AGCAGCGAATTCTCAGCGGACATCGTCAGT SEQ ID NO:24 | 546 | 227 |

[a]Promoter sequences are available in Genbank.
[b]The underlined region of the upper primer is BamHI restriction enzyme cleavage site. 3' to the restriction site is sequence (generally 18 nucleotides) complimentary the region upstream of the desired promoter.
[c]The underlined region of the lower primer is an EcoRI restriction enzyme cleavage site. 3' to the restriction site is sequence (generally 18 nucleotides) complimentary to the region downstream of the desired promoter.
[d]The template for PCR reactions was either a chromosomal DNA preparation (C, prepared according Zyskind & Bernstein, Recombinant DNA Laboratry Manual, Academic Press, New York, 1992) or a water-resuspended plaque from one of an overlapping set of specialized λ transducing phages coveringthe E. coli chromosome [Kohara et al. Cell 50; 495–508 (1987)] indicated by its assigned number [see Bouffard et al., CABIOS 8: 563–567 (1992)] growth on E. coli K12.Amplification from plaques was performed by the method of Berg [Krishnan, Blakesley and Berg (1992) Nucleic Acids Reaseacrh 19: 1153] while that from the chromosmal preparation differed from that of Berg that 1 µl of the chromosomal DNA preparation was used as template.
[e]The calculated size of the PCR product. Agarose gel electrophoretic analysis confirmed product size.

All of the promoter sequences listed in Table IV are published and available from GenBank. The underlined region of the upper primer is a BamHI restriction enzyme cleavage site. 3' to the restriction site is sequence (generally 18 nucleotides) complimentary to the region upstream of the desired promoter. The underlined region of the lower primer is an EcoRI restriction enzyme cleavage site. 3' to the restriction site is sequence (generally 18 nucleotides) complementary to the region downstream of the desired promoter. The template for PCR reactions was either a chromosomal DNA preparation (C, prepared according to Zyskind & Bernstein, *Recombinant DNA Laboratory Manual*, Academic Press, New York, 1992) or a water resuspended plaque from one of an overlapping set of specialized λ transducing phages covering the *E. coli* chromosome (Kohara et al., *Cell* 50; 495–508 (1987)) indicated by its assigned number (Bouffard et al., *CABIOS* 8: 563–567 (1992)) grown on *E. coli* K12. Amplification from plaques was performed by the method of Berg et al., *Nucleic Acids Research* 19,1153, (1991) Amplifications from the chromosomal preparations differed from that of Berg in that 1 μL of the chromosomal DNA preparation was used as template. The calculated size of the PCR product was confirmed by agarose gel electrophoresis.

Each of the resultant plasmids were placed in three *E. coli* host strains: RFM443, DE112, and W3110. Plasmids and transformed host cells are listed below in Table V.

TABLE V

| Promoter | Plasmids | E. coli host | Strain name |
| --- | --- | --- | --- |
| lon | pLonE6 | W3110 | pLonE6/W3110 |
|  | pLonE6 | RFM443 | pLonE6/RFM443 |
|  | pLonE6 | DE112 | pLonE6/DE112 |
|  | pLonF1 | W3110 | pLonF1/W3110 |
|  | pLonF1 | RFM443 | pLonF1/RFM443 |
|  | pLonF1 | DE112 | pLonF1/DE112 |
| recA | pRecALux1 | W3110 | DPD2789 |
|  | pRecALux2 | W3110 | DPD2790 |
|  | pRecALux3 | W3110 | DPD2791 |
|  | pRecALux1 | RFM443 | DPD2792 |
|  | pRecALux2 | RFM443 | DPD2793 |
|  | pRecALux3 | RFM443 | DPD2794 |
|  | pRecALux1 | DE112 | DPD2795 |
|  | pRecALux2 | DE112 | DPD2796 |
|  | pRecALux3 | DE112 | DPD2797 |
| uvrA | pUvrALux1 | W3110 | DPD2814 |
|  | pUvrALux2 | w3110 | DPD2815 |
|  | pUvrALux3 | W3110 | DPD2816 |
|  | pUvrALux4 | W3110 | DPD2817 |
|  | pUvrALux1 | RFM443 | DPD2818 |
|  | pUvrALux2 | RFM443 | DPD2819 |
|  | pUvrALux3 | RFM443 | DPD2820 |
|  | pUvrALux4 | RFM443 | DPD2821 |
|  | pUvrALux1 | DE112 | DPD2622 |
|  | pUvrALux2 | DE112 | DPD2823 |
|  | pUvrALux3 | DE112 | DPD2824 |
|  | pUvrALux4 | DE112 | DPD2825 |
| katG | pKatGLux2 | W3110 | DPD2507 |
|  | pKatGLux6 | W3110 | DPD2508 |
|  | pKatGLux2 | DE112 | DPD2509 |
|  | pKatGLux6 | DE112 | DPD2510 |
|  | pKatGLux2 | RFM443 | DPD2511 |
|  | pKatGLux6 | RFM443 | DPD2512 |
| micF | pMicFLux1 | W3110 | DPD2515 |
|  | pMicFLux2 | W3110 | DPD2516 |
|  | pMicFLux1 | DE112 | DPD2517 |
|  | pMicFLux2 | DE112 | DPD2518 |
|  | pMicFLux1 | RFM443 | DPD2519 |
|  | pMicFLux2 | RFM443 | DPD2520 |
| uspA | pUspALux.2 | W3110 | DE130 |
|  | pUspALux.2 | RFM443 | DE134 |
|  | pUspALux.2 | DE112 | DE138 |
|  | pUspALux.6 | W3110 | DE142 |
|  | pUspALux.6 | RFM443 | DE146 |
|  | pUspALux.6 | DE112 | DE150 |

TABLE V-continued

| Promoter | Plasmids | E. coli host | Strain name |
| --- | --- | --- | --- |
|  | pUspALux.13 | W3110 | DE154 |
|  | pUspALux.13 | RFM443 | DE158 |
|  | pUspALux.13 | DE112 | DE162 |
| xthA | pXthALux1 | W3110 | DPD2771 |
|  | pXthALux2 | W3110 | DPD2772 |
|  | pXthALux3 | W3110 | DPD2773 |
|  | pXthALux4 | W3110 | DPD2774 |
|  | pxthALux5 | W3110 | DPD2775 |
|  | pXthALux6 | W3110 | DPD2776 |
|  | pXthALux1 | RFM443 | DPD2777 |
|  | pXthALux2 | RFM443 | DPD2778 |
|  | pXthALux3 | RFM443 | DPD2779 |
|  | pXthALux4 | RFM443 | DPD2780 |
|  | pXthALux5 | RFM443 | DPD2781 |
|  | pXthALux6 | RFM443 | DPD2782 |
|  | pXthALux1 | DE112 | DPD2783 |
|  | pXthALux2 | DE112 | DPD2784 |
|  | pXthALux3 | DE112 | DPD2785 |
|  | pXthALux4 | DE112 | DPD2786 |
|  | pXthALux5 | DE112 | DPD2787 |
|  | pXthALux6 | DE112 | DPD2788 |
| his | pHisLux5 | RFM443 | DPD1534 |
|  | pHisLux9 | RFM443 | DPD1535 |
|  | pHisLux12 | RFM443 | DPDI536 |
|  | pHisLux5 | W3110 | DPD1537 |
|  | pHiSLux9 | W3110 | DPD1538 |
|  | pHiSLux12 | W3110 | DPD1539 |
|  | pHiSLux5 | DE112 | DPD1540 |
|  | pHiSLux9 | DE112 | DPD1541 |
|  | pHisLux12 | DE112 | DPD1542 |
| lac | pLacLux | W3110 | TV1063 |
|  | pLacLux | RFM443 | TV1058 |
|  | pLacLux | RFM443 | TV1068 |
|  | pLacLux | DE112 | TV1073 |
| phoA | pPhoALux3 | W3110 | DPD1522 |
|  | pPhoALux4 | W3110 | DPD1523 |
|  | pPhoALux5 | W3110 | DPD1524 |
|  | pPhoALux11 | W3110 | DPD1525 |
|  | pPhoALux3 | RFM443 | DPD1526 |
|  | pPhoALux4 | RFM443 | DPD1527 |
|  | pPhoALux5 | RFM443 | DPD1528 |
|  | pPhoALux11 | RFM443 | DPD1529 |
|  | pPhoALux3 | DE112 | DPD1530 |
|  | pPhoALux4 | DE112 | DPD1531 |
|  | pPhoALux5 | DE112 | DPD1532 |
|  | pPhoALux11 | DE112 | DPD1533 |
| glnA | pGlnALux1 | W3110 | DPD2830 |
|  | pGlnALux2 | W3110 | DPD2831 |
|  | pGlnALux3 | W3110 | DPD2832 |
|  | pGlnALux4 | W3110 | DPD2833 |
|  | pGlnALux1 | RFM443 | DPD2834 |
|  | pGlnALux2 | RFM443 | DPD2835 |
|  | pGlnALux3 | RFM443 | DPD2836 |
|  | pGlnALux4 | RFM443 | DPD2837 |
|  | pGlnALux1 | DE112 | DPD2838 |
|  | pGlnALux2 | DE112 | DPD2839 |
|  | pGlnALux3 | DE112 | DPD2840 |
|  | pGlnALux4 | DE112 | DPD2841 |

Promoter-reporter fusions were tested in transformed detector host cells using a variety of environmental insults, appropriate to the known sensitivity of the promoter. Promoters and their corresponding inducing insults are summarized in Table VI.

TABLE VI

| Target Promoter | Upset[b] | Observed Induction by[c] | Expression lacking in[d] |
| --- | --- | --- | --- |
| lon | protein damage | ethanol[e], copper sulfate |  |
| recA | DNA damage | mitomycin C[f], cadmium chloride[g], U.V. light ethidium bromide |  |

TABLE VI-continued

| Target Promoter | Upset[b] | Observed Induction by[c] | Expression lacking in[d] |
|---|---|---|---|
| uvrA | DNA damage | U.V. light | |
| katG | oxidative damage | methyl viologen[h], hydrogen peroxide[i], menadione[h] | |
| micF | oxidative damage | methyl viologen, hydrogen peroxide | |
| uspA | any | ethanol[j], copper sulfate | |
| xthA | stationary phase | acetate, propionate, hydrogen peroxide | |
| his | amino acid starvation | serine hydroxamate[k] | relA spoT |
| lac | carbon starvation | absence of glucose as a C source[l] | |
| phoA | phosphate limitation | low phosphate levels[m] | |
| glnA | nitrogen limitation | glutamine as sole N source[n] | |

[b]causing a pleiotropic regulatory response.
[c]chemical induction turning on an increased bioluminescent response.
[d]genetic construction preventing bioluminescent expression by disruption of a positive regulatory circuit.
[e]ethanol is a strong inducer of the heat shock response [Niedhardt and VanBogelen in *E. coli* and *Salmonella typhimurium*; Cellular and Molecular Biology (Neidhardt, F. C. et al. Eds., pp. 1334–1345, American Society of Microbiology, Washington, DC (1987)]
[f]mitomycin C is a known inducer of the SOS response [Walker in *E. coli* and *Salmonella typhimurium*; Cellular and Molecular Biology (Neidhardt, F. C. et al. Eds., pp. 1346–1357, American Society of Microbiology, Washington, DC (1987)].
[g]cadmium had been reported to induce genetic damage [Neidhardt and VanBogelen in *E. coli* and *Salmonella typhimurium*; Cellular and Molecular Biology (Neidhardt, F. C. et al. Eds., pp. 1334–1345, American Society of Microbiology, Washington, DC (1987)].
[h]this compound promotes redox cycling producing superoxide. Superoxide is dismutated to hydrogen peroxide. Superoxide induces synthesis of 40 proteins in addition to the 40 proteins induced by exposure to hydrogen peroxide [Demple, Ann. Rev. Genet. 25: 315–337 (1991)].
[i]hydrogen peroxide induces the oxyR regulon and several other proteins among the approximately 40 polypeptides induced in *E. coli* and *S. typhimurium* [Christman et al. Cell 41: 753–762 (1985); Storz et al. Science 248: 189–194 (1990); Demple, Ann. Rev. Genet. 25: 315–337 (1991)].
[j]T. Van Dyk, unpublished.
[k]this chemical prevents aminoacylation of tRNA[*] thus inducing the stringest response [Cashel and Rudd in *E. coli* and *Salmonella typhimurium*; Cellular and Molecular Biology (Neidhardt, F. C. et al. Eds., pp. 1410–1438, American Society of Microbiology, Washington, DC (1987); Winkler in *E. coli* and *Salmonella typhimurium*; Cellular and Molecular Biology (Neidhardt, F. C. et al. Eds., pp. 395–411, American Society of Microbiology, Washington, DC (1987)].
[l]the catabolite activation response is triggered by the absence of a good carbon source [Neidhardt, Ingraham and Schaecter. Physiology of the Bacterial Cell: A Molecular Approach, Sinauer Associates, Sunderland, MA (1990), pp. 351–388; Magasanik and Neidhardt in *E. coli* and *Salmonella typhimurium*; Cellular and Molecular Biology (Neidhardt, F. C. et al. Eds., pp. 1318–1325, American Society of Microbiology, Washington, DC (1987)].
[m]use of limiting phosphate concentrations induces the phosphate starvation regulon [Wanner in *E. coli* and *Salmonella typhimurium*; Cellular and Molecular Biology (Neidhardt, F. C. et al. Eds., pp. 1326–1333, American Society of Microbiology, Washington, DC (1987)].
[n]use of glutamine as a sole N source induces expression of the N starvation regulon [Rietzer and Magasanik in *E. coli* and *Salmonella typhimurium*; Cellular and Molecular Biology (Neidhardt, F. C. et al. Eds., pp. 1302–1320, American Society of Microbiology, Washington, DC (1987)].

Example 11

Response of lon Transformed Host Cell to Ethanol or Copper Sulfate

*E. coli* strain pLonE6/RFM443 was grown overnight at 26° C. in LB medium containing Kanamycin (50 μg/mL) and diluted into the fresh LB medium containing Kanamycin (50 μg/mL) and grown at 26° C. to early log-phase. 50 μL of cells were added to 50 μL of LB medium containing Kanamycin (50 μg/mL) and various concentrations of etha- nol (added directly to the medium) or copper sulfate (diluted from a 250 mM stock solution in water). Light output was quantitated as a function of incubation time in a Dynatech ML3000 luminometer at 26° C. The maximum response induced by ethanol was observed when the final concentration of ethanol was 4%; at 60 min after addition of ethanol the luminescence was 134 fold greater in the presence of ethanol than in the untreated control. The maximum copper sulfate induction resulted when the final concentration was 5 mM; at 60 min the induction ratio was 408 fold.

Example 12

Response of recA Transformed Host Cell to Mitomycin C, Ethidium Bromide or Cadmium Chloride

*E. coli* strains containing plasmid pRecALux3 were grown overnight at 26° C. in LB medium containing Kanamycin (50 μg/mL) and diluted into the fresh LB medium containing Kanamycin (50 μg/mL) and grown at 26° C. to early log-phase. 50 μL of cells were added to 50 μL of LB medium containing Kanamycin (50 gg/mL) and various concentrations of mitomycin C (diluted from a 2 mg/ml stock solution in water). Light output was quantitated in a Dynatech ML3000 luminometer at 26° C. At 100 min after addition of 0.5 μg/mL mitomycin C, the induction ratios were as follows:

| Strain DPD2791 | (pRecALux3/W3110) | 4.74 |
| Strain DPD2794 | (pRecALux3/RFM443) | 20.00 |
| Strain DPD2797 | (pRecALux3/DE112) | 15.70 |

*E. coli* strain DPD2794 demonstrated response to the presence of ethidium bromide. Cells were grown overnight at 26° C. in LB medium containing kanamycin (25 μg/mL) and diluted into the fresh LB medium and grown at 26° C. to early log-phase. 50 gL of cells were added to 50 gL of LB medium containing various concentrations of ethidium bromide (diluted from a 10 mg/mL stock solution in water). Light output was quantitated in a Dynatech ML3000 luminometer at 26° C. At 180 min after addition of 0.25 mg/mL ethidium bromide, the induction ratio was 1.9 fold.

*E. coli* strain DPD2794 was also shown to respond to the presence of cadmium chloride by a disk diffusion assay. Cells were spread on an LB agar plate containing Kanamycin (50 μg/mL) and a filter disk which had been wet with 20 gl of a 100 mM cadmium chloride solution was placed on the agar plate. Following incubation overnight at 37° C., the agar plate was allowed to cool to room temperature. DuPont Reflection® film was exposed to the plate for 10 min. Surrounding a zone of growth inhibition (18 mm diameter) a zone of enhanced bioluminescence (35 mm diameter) was observed.

Example 13

Response of KatG Transformed Host Cell to Methyl Viologen, Hydrogen Peroxide or Menadione

*E. coli* strains containing plasmids pKatGLux2 and pKat-GLux6 were grown overnight at 37° C. in LB medium and diluted into fresh LB medium and grown at 37° C. to early log-phase. 40 μL of cells were added to 60 μL of LB medium and various concentrations of methyl viologen (MV) which was diluted from a 200 mg/mL stock solution in water or hydrogen peroxide ($H_2O_2$) which was diluted from a 0.3% solution in water. Light output was quantitated in a Dynatech ML3000 luminometer at 26° C. Data is shown below in Tables VII and VIII.

TABLE VII

| Strain | Time of Max Ind. | [MV] for Max Ind. | Induction Ratio |
| --- | --- | --- | --- |
| DPD2507 | 60 min | 8.75 mM* | 56.7 |
| DPD2508 | 60 min | 8.75 mM* | 19.5 |
| DPD2509 | 60 min | 8.75 mM* | 31.9 |
| DPD2510 | 80 min | 8.75 mM* | 11.2 |
| DPD2511 | 60 min | 8.75 mM* | 226 |
| DPD2512 | 50 min | 2.2 mM | 50.7 |

*Maximum concentration tested.

TABLE VIII

| Strain | Time of Max Ind. | [$H_2O_2$] for Max Ind. | Induction Ratio |
| --- | --- | --- | --- |
| DPD2507 | 65 min | 1.65 mM | 70.5 |
| DPD2508 | 65 min | 1.65 mM | 3034 |
| DPD2509 | 55 min | 0.41 mM | 250 |
| DPD2510 | 50 min | 0.41 mM | 810 |
| DPD2511 | 55 min | 0.41 mM | 376 |
| DPD2512 | 45 min | 0.41 mM | 6067 |

*E. coli* strain DPD2511 was also shown to respond with increased bioluminesence to the presence of menadione. Cells were grown overnight in LB medium containing kanamycin (25 µg/mL) at 26° C. and diluted to LB medium and grown to log-phase at 26° C. 20 µL of cells were added to wells of microtiter plates containing various concentrations of menadione (diluted from a 200 mg/mL solution in water) in 80 µL of LB medium. Light output was quantitated in a Dynatech ML3000 luminometer at 26° C. At 80 min the bioluminescence of cells treated with 2.3 mM menadione was 1200-fold greater than in the untreated control.

Example 14

Response of MicF Transformed Host Cell to Methyl Viologen or Hydrogen Peroxide

*E. coli* strains containing plasmids pMicFLux1 and pMicFLux2 were grown overnight at 37° C. in LB medium and diluted into the fresh LB medium and grown at 37° C. to early log-phase. 40 µL of cells were added to 60 µL of LB medium and various concentrations of methyl viologen (diluted from a 200 mg/mL stock solution in hydrogen hydrogen peroxide (diluted from a 0.3% solution in water). Light output was quantitated in a Dynatech ML3000 luminometer at 26° C. Data is shown below in Tables IX and X.

TABLE IX

| Strain | Time of Max Ind. | [MV] for Max Ind. | Induction Ratio |
| --- | --- | --- | --- |
| DPD2515 | 120 min# | 2.2 mM | 99.9 |
| DPD2516 | 50 min | 8.75 mM* | 14.7 |
| DPD2517 | 120 min# | 2.2 mM | 1.8 |
| DPD2518 | 120 min# | 2.2 mM | 1.4 |
| DPD2519 | 120 min# | 2.2 mM | 87.5 |
| DPD2520 | 120 min# | 2.2 mM | 69.2 |

Longest induction time analyzed.
*Maximum concentration tested.

TABLE X

| Strain | Time of Max Ind. | [$H_2O_2$] for Max Ind. | Induction Ratio |
| --- | --- | --- | --- |
| DPD2515 | 65 min | 1.65 mM | 47.5 |
| DPD2516 | 40 min | 0.41 mM | 5035 |
| DPD2517 | 80 min | 1.65 mM | 4.2 |
| DPD2518 | 80 min | 1.65 mM | 1.6 |
| DPD2519 | 60 min | 1.65 mM | 2.2 |
| DPD2520 | 60 min | 1.65 mM | 2.6 |

Example 15

Response of UspA Transformed Host Cell to Ethanol or Copper Sulfate

*E. coli* strain DE134 containing plasmid pUspALux.2 was grown overnight at 26° C. in LB medium containing Kanamycin (50 µg/mL) and diluted into the fresh LB medium containing Kanamycin (50 µg/mL) and grown at 26° C. to early log-phase. 50 µL of cells were added to 50 µL of LB medium containing Kanamycin (50 µg/mL) and various concentrations of ethanol (added directly to the medium) or copper sulfate (diluted from a 250 mM stock solution in water). Light output was quantitated in a Dynatech ML3000 luminometer at 26° C. The maximum response induced by ethanol was observed when the final concentration of ethanol was 4%; at 60 min after addition of ethanol the induction ratio was 148 fold. The maximum copper sulfate induction resulted when the final concentration was 5 mM; at 60 min the induction ratio was 6.9 fold.

Example 16

Response of xthA Transformed Host Cell to Propionate, Acetate or Hydrogen Peroxide

*E. coli* strains containing plasmids with the xthA promoter fused to the lux operon were grown overnight at 26° C. in LB medium containing Kanamycin (25 µg/mL) and diluted into the fresh LB medium containing Kanamycin (25 µg/mL) and grown at 26° C. to early log-phase. 50 µL of cells were added to 50 µL of LB medium containing Kanamycin (25 µg/mL) and various concentrations of acetate (diluted from a 2M stock solution in water), propionate (diluted from a 2M stock solution in water), or hydrogen peroxide (diluted from a 30% stock solution in water). Light output was quantitated in a Dynatech ML3000 luminometer at 26° C. At 9 h after addition of 0.025% hydrogen peroxide to strain DPD2778, the bioluminescence was 70-fold greater than in the control with no addition; at 1 d after addition of 100 mM acetate, the induction ratio was 54; and at 3 d after addition of 100 mM propionate the response ratio was 207. For strain DPD2781, at 18 h after the addition of 0.05% hydrogen peroxide the bioluminescence was 660-fold greater than in the control with no addition; at 1 day after addition of 100 mM acetate, the induction ratio was 61; and at 3 d after addition of 100 mM propionate the induction ratio was 291.

Example 17

Response of His Transformed Host Cell to Gene Expression

*E. coli* strains containing plasmids with the his promoter fused to the lux operon were shown to be regulated by the stringent response system in a genetic experiment showing the dependence of gene expression on the presence of the appropriate regulatory elements. Plasmid DNA was placed by $CaCl_2$ mediated transformation into otherwise isogenic strains, with normal regulation (strain CF1648), mutated in the relA regulatory gene (strain CF1693), or mutated in both the relA and spot regulatory genes (strain 1651). These strains were obtained from M. Cashel (Xiao et al. (1991) Residual Guanosine 3'5'-bispyrophosphate synthetic activity of relA null mutants can be eliminated by spoT null mutations. J. Biol. Chem., 266: 5980-5990). The strains were grown in LB medium containing Ampicillin (150 µg/mL) overnight at 37° C. and diluted in the same medium and grown at 37° C. until early log-phase. Luminescence was quantitated in a Dynatech ML3000 luminometer at 26° C. Three plasmids each demonstrated reduced bioluminesence in a relA mutant, and dramatically reduced bioluminesence in the relA, spot double mutant. Data is shown below in Table XII.

TABLE XII

| Plasmid | Host strain genotype | Fold reduction in bioluminescence |
|---|---|---|
| pHisLux5 | relA$^+$ spoT$^+$ | 1X |
| pHisLux5 | relA$^-$ spoT$^+$ | 5.7X |
| pHisLux5 | relA$^-$ spoT$^-$ | 137X |
| pHisLux9 | relA$^-$ spoT$^+$ | 1X |
| pHisLux9 | relA$^-$ spoT$^+$ | 4.4X |
| pHisLux9 | relA$^-$ spoT$^-$ | 351X |
| pHisLux12 | relA$^+$ spoT$^+$ | 1X |
| pHisLux12 | relA$^-$ spoT$^+$ | 4.5X |
| pHisLux12 | relA$^-$ spoT$^-$ | 196X |

These fusions could also be induced by exposure to serine hydroxamate. This compound is a specific inhibitor of tRNA$^{ser}$ aminoacylation by seryl-tRNA synthetase [Pizer and Tosa (1971) J. Bacteriol. 106:972-982]. Cells were grown overnight with shaking at 29° C. in minimal E medium (Davis et al., Advanced Bacterial Genetics, Cold Spring Harbor Laboratory, Cold Spring Harbor, N.Y., 1980) supplemented with uracil (25 µg/mL), kanamycin sulfate (10 µg/mL) and glucose (0.4%). The cells were diluted 20 fold in the same medium modified only by omission of kanamycin sulfate and grown as noted above to between 19 and 34 Klett Units. A 2 mg/mL solution of D,L-serine hydroxamate in water was diluted (serial 2-fold dilutions) in the same medium modified only by omission of kanamycin sulfate. These dilutions (50 µL) were mixed with 50 µL of actively growing cultures in a microtiter plate. Light output was quantitated in a Dynatech ML3000 luminometer at 26° C. After 1180 min of incubation the following induction ratios were observed:

TABLE XIII

| Strain | Description | [Ser. Hyd.] for Max Ind. | Induction Ratio |
|---|---|---|---|
| DPD1534 | pHisLux5/RFM443 | 250 µg/mL | >2000 |
| DPD1535 | pHisLux9/RFM443 | 250 µg/mL | >1000 |
| DPD1536 | pHisLux12/RFM443 | 250 µg/mL | >400 |
| DPD1540 | pHisLux5/DE112 | 250 µg/mL | 9 |
| DPD1541 | pHisLux9/DE112 | 250 µg/mL | 3 |
| DPD1542 | pHisLux12/DE112 | 250 µg/mL | 1 |

This data implies that we have capitalized upon the knowledge of the stringent response mechanism to develop a biosensor capable of detecting a wide range of amino acid biosynthetic inhibitors. Since many herbicides are inhibitors of amino acid biosynthesis, this biosensor may be a useful detector of several herbicides [e.g., acetolactate synthase-directed herbicides (including those in the sulfonylurea, imidazolinone, and triazolo- pyrimidine classes), phosphinothricin and glyphosate].

Example 18

Response of phoA Transformed Host Cell to Limiting Phosphate

E. coli strains DPD1522 through DPD1533 containing plasmids with the phoA promoter fused to the lux operon were shown to respond to limiting phosphate. These strains were streaked for single colonies on MOPS media (Bochner et al. (1982) Complete analysis of cellular nucleotides by two-dimensional thin layer chromatography, J. Biol. Chem. 257: 9759-9769) lacking tricine and containing glucose (0.4%) as the carbon source, vitamin B1 (0.00002%), and a standard concentration of phosphate (2.0 mM) or a limiting concentration of phosphate (0.1 mM). Following overnight incubation at 37° C., the plates were allowed to cool to room temperature and were exposed to DuPont Reflections® film for various amounts of time. The strains growing on the standard concentration of phosphate required 3 h to result in significant exposure of the film. In contrast, the strains growing on limiting phosphate media required only 1 min to yield significant exposure of the film, thus demonstrating induction of bioluminesence by a limiting phosphate source.

This result was confirmed by an experiment conducted with a luminometer. Cultures were grown overnight with shaking at 29° C. in the above minimal medium containing 2 mM potassium phosphate supplemented with glucose (0.4%) uracil (25 µg/mL) and kanamycin sulfate (10 µg/mL). Cells were collected by centrifugation prior to resuspension in an equal volume of the same medium modified only by the omission of kanamycin sulfate and potassium phosphate. 50 µL of cells were added to 50 µL of the same medium lacking kanamycin sulfate and modified to give a final concentrations of potassium phosphate that ranged from 0-2000 uM. Light output was quantitated in a Dynatech ML3000 luminometer at 26° C. as a function of time for more than 300 min after addition of the resuspended cells. Typical results for two strains [DPD1522 (pPhoALux3/W3110) and DPD1523 (pPhoALux4/W3110)] are presented below:

TABLE XIV

| Strain | uM Phosphate | Maximal Induction Ratio | Initial Induction Time (min)* |
|---|---|---|---|
| DPD1522 | 0 | 1000 | 20 |
| | 31 | 500 | 50 |
| | 63 | 400 | 180 |
| | 125 | 3 | 260 |
| | 250 | ni | ni |
| | 500 | ni | ni |
| | 1000 | ni | ni |
| | 2000 | ni | ni |
| DPD1523 | 0 | >900 | 20 |
| | 31 | 700 | 20 |
| | 63 | 400 | 125 |
| | 125 | 350 | 175 |

TABLE XIV-continued

| Strain | uM Phosphate | Maximal Induction Ratio | Initial Induction Time (min)* |
|---|---|---|---|
| | 250 | ni | ni |
| | 500 | ni | ni |
| | 1000 | ni | ni |
| | 2000 | ni | ni | ni: induction not observed
*time of measurable increase in luminesence over baseline reading

Example 19

Response of glnA Transformed Host Cell to Glutamine as a Sole Nitrogen Source E. coli strain DPD2831 was grown overnight in minimal phosphate medium (Bender et al., (1977) Biochemical parameters of glutamine synthetase from Klebsiella aerogenes, J. Bacteriol, 129: 1001–1009) containing 0.1% $(NH_4)_2SO_4$. These cultures were collected by centrifugation and resuspended in either the same medium (control) or in that medium lacking $(NH_4)_2SO_4$, but containing 0.004% glutamine as the sole nitrogen source. Luminescence was quantitated in a Dynatech ML3000 luminometer at 26° C. At 62 min after resuspension the cells in the medium with the poor nitrogen source (glutamine) had 62-fold greater bioluminesence than did the control culture.

Example 20

Construction of lac Containing Plasmids and Host Cells

E. coli strains were constructed such that plasmid-borne lux genes of Vibrio fischeri were under control of the E. coli lac promoter. A 232 basepair Pvu II to Eco RI fragment of pUC19 (Yanisch-Perron et al., (1985) Improved M13 phage cloning vectors and host strains: nucleotide sequences of the M13mp18 and pUC19 vectors, Gene 33: 103–119) was ligated into Sma I and EcoRI digested pUCD615 (Rogowsky et al., (1987) Regulation of the vir genes of Agrobacterium tumefaciens plasmid pTiC58, J. Bacteriol, 169: 5101–5112) to yield pLacLux. This plasmid was originally isolated in E. coli strain XL1-Blue (Bullock et al. (1987), XL1-Blue: A high efficiency plasmid transforming recA Escherichia coli strain with beta-galactosidase selection, Biotechniques, 4: 376–379) which contains an F'lacI$^q$, so that the genes were inducible by IPTG. The plasmid was also placed by $CaCl_2$ mediated transformation into E. coli strains W3110, RFM443, and DEll2 (see Table V, Example 10).

Example 21

Response of lac Transformed Host Cell to Carbon Source Levels

Glucose is the preferred carbon source for E. coli. E. coli strains TV1058 and TV1068 each containing the plasmid pLacLux were grown overnight in LB medium containing kanamycin (25 µg/mL) either lacking or containing 0.4% glucose at 26° C. The overnight cultures were diluted and grown to early log phase in the same media as the overnight culture. Culture turbidity was measured with a Klett-Summerson colorimeter with a #66 red filter. Luminescence present in 50 µL of cell culture was quantitated in a Dynatech ML3000 luminometer at 26° C. Data are given below in Table XIV.

TABLE XV

| Strain | Media | Klett Units | RLU/50 µL cells |
|---|---|---|---|
| TV1058 | −glucose | 18 | 32.4 |
| TV1058 | +glucose | 22 | 0.087 |
| TV1068 | −glucose | 21 | 29.1 |
| TV1068 | +glucose | 21 | 0.084 |

Thus, cells containing the plasmid pLacLux increase bioluminescence when grown on the suboptimal carbon sources present in LB medium.

Example 22

Construction and Response of fabA Transformed Host Cell to Fatty Acid Starvation The fabA gene encodes the enzyme responsible for the placement of a double bond in the fatty acids and hence membrane of E. coli. Such double bonds are an absolute requirement for growth. Synthesis of fabA is directed by two promoter elements: a low level, constitutive upstream and an inducible downstream promoter. The location of the two promoters in the sequence surrounding fabA has been determined. The PCR primers shown in Table IV are designed to allow cloning of the inducible downstream promoter without the constitutive upstream promoter. The transcription of the downstream promoter can be modulated at least 10 fold at the RNA level (Henry et al., J. Mol. Biol. 222:843–849 (1991)). Control of the dual fabA promoters, studied in fabA-lac fusions, has shown a 13 fold modulation at the level of β-galactosidase specific activity (Henry et al., Cell, 70: 671–679 (1992)). Control of fabA expression is mediated by the fadR gene product (Nunn et al., J. Bacteriol, 154:554–560 (1983)). The FadR protein stimulates fabA transcription by binding to the −40 region of the regulated, downstream fabA promoter. If there is an excess of membrane synthetic capacity, long-chained acyl-CoA molecules accumulate. These molecules bind to the FadR protein, dissociating it from the regulated fabA promoter (Henry et al., Cell, 70: 671–679 (1992)). The fabA-lux fusion is thus expected to serve as a monitor of the state of membrane synthesis. Under conditions of fatty acid starvation, long chain acyl-CoA pools will be low and expression of fabA-lux should be high; excess fatty acids should result in large pools of long chain acyl-CoAs and hence low levels of lux expression from the fusion. This fusion should monitor not only fatty acid synthetic inhibition but CoA availability, which can be limited by many factors including inhibition of the isoleucine-valine synthetic enzyme acetolactate synthase (LaRossa et al., pp. 108–121 in Biosynthesis of Branched Chain Amino Acids, ed. by Barak, Chipman and Schloss, VCH Publishers, New York, 1990). Methods of producing the stress of fatty acid starvation on a potential detector orgasm containing a fabA::lux fusion might include inhibition of fatty acid desaturation by inclusion of 3-decenoyl-N-acetylcysteamine in the growth medium (Nunn et al., (1983) *J. Bacteriol*, 154:554–560) or the sequestering of intracellular CoA as propionyl-CoA by the action of the herbicides such as sulfometuron methyl (Van Dyk et al., *Mol Gen Genet* (1987) 207:435–440) or the amino acid valine (LaRossa et al., (1987) *J. Bacteriol*, 169:1372–1378).

Construction of fabALux and Transformation of RFM443

Construction of a transforming plasmid containing the fabA::lux gene fusion is prepared using methods and materials essentially as described in Example 3 for the preparation of pRY001 and pRY002. PCR amplification of the fabA promoter is accomplished with the primers listed in Table IV. The sequence of the fabA gene is known and is readily available from the Genbank database of nucleic acid sequences. The plasmid carrying the fabA::lux fusion is referred to as pFabALux.

*E. coli* host RFM443 is transformed with the pFabALux in using the materials and methods described for the construction of WM1021 and WM1202 in Example 3.

*E. coli* host RFM443 is transformed with the pFabALux is grown overnight in minimal E medium containing kanamycin (10 µg/mL) at 29° C. The overnight cultures are diluted and grown to early log phase in the same media as the overnight culture. Culture turbidity is measured with a Klett-Summerson colorimeter with a #66 red filter. Luminescence present in 50 µL of cell culture in the presence or absence of 50 µg/mL of sulfometuron methyl is quantitated in a Dynatech ML3000 luminometer at 26° C. It is seen that cultures in the presence of sulfometuron methyl demonstrate a 10–25 fold increase in luminesces when compared with cultures in the absence of sulfometuron methyl.

light irradiation. All but grpE::lux responded to this physical challenge by increasing bioluminescence. Strains were grown overnight with shaking in LB medium supplemented with kanamycin sulfate (25 µg/mL) at 26° C. After 20-fold dilution into LB medium, culture was continued with shaking at 26° C. until densities of 20–40 Klett units were reached. Cultures (50 µl) and fresh LB medium (50 µl) were added to wells of a microtiter plate prior to irradiation at 254 nm with a Stratalinker 1800 instrument (Stratagene). Subsequently, light output was quantitated as a function of time after irradiation in a Dynatech ML3000 luminometer at 26° C. Response ratios were calculated after 240 min of incubation. They are reported in the Table XVI:

TABLE XVI

| | Response Ratio: | | | | | | |
|---|---|---|---|---|---|---|---|
| Dose (mjoule/cm$^2$) | DPD2794 (pRecAlux3/ RFM443) | DPD2815 pUvrALux2/ W3110 | TV1061 (pGrpElux.5/ RFM443) | WM1202 [pRY002/RFM443 dnaK fusion)] | DPD2507 (pKatGLux2/ W3110) | DPD2515 (pMicFLux1/ W3110) | DE158 (pUspALux13/ RFM443) |
| 0 | =1 | =1 | =1 | =1 | =1 | =1 | =1 |
| 0.1 | 1 | 1 | 1 | 1 | 1 | 1 | 1 |
| 0.4 | 2 | 2 | 1 | 2 | 1 | 1 | 1 |
| 2 | 5 | 14 | 1.2 | 5 | 1.2 | 1.5 | 2 |
| 10 | 10 | 29 | 1.5 | 20 | 2 | 4 | 2.5 |
| 50 | 15 | 57 | 1.5 | 30 | 2.5 | 7 | 3 |
| 250 | 15 | 63 | <1 | 25 | 3 | 10 | 5 |
| 1250 | 19 | 76 | <1 | 20 | 2.5 | 10 | 8 |

Thus, cells containing the plasmid pFabALux are expected to increase bioluminescence when grown under conditions of fatty acid synthesis inhibition.

Example 23

Responses to a Physical Challenge

The recA::lux, uvrA:lux, grpE::lux, dnaK::lux, katG::lux, micF::lux and uspA::lux fusions were exposed to ultraviolet It is apparent that all but one of the tested constructs responded to physical as well as chemical stresses.

We claim:

1. A method of detecting the presence of an environmental insult comprising:

(a) exposing a transformed detector *E. coli* to an environmental insult, the transformed detector *E. coli* being genetically engineered to contain an expressible heterologous luxCDABE gene complex under the control of a stress-inducible promoter sequence wherein the promoter sequence is responsive to a regulatory circuit; and (b) measuring an increase in luminescence of the transformed detector *E. coli*, the increase indicating the presence of an environmental insult.

2. A method of detecting stress in a population of transformed *E. coli* comprising:

(a) exposing a population of transformed detector *E. coli* to an environmental insult, the transformed detector *E. coli* being genetically engineered to contain an expressible heterologous luxCDABE gene complex trader the control of a stress-inducible promoter sequence wherein the promoter sequence is responsive to a global regulatory circuit; and b) measuring an increase in luminescence of the transformed detector *E. coli*, the increase indicating stress.

3. The method of claim 1 or 2 further comprising correlating the increase in luminescence to the level of environmental insult present.

4. The method of claim 1 or 2 whereto the environmental insult is sublethal.

5. The method of claim 1 or 2 wherein the environmental insult is selected from the group consisting of atrazine, benzene, copper sulfate, 2,4-dichlorophenoxy acetic acid, ethanol, methanol, 2-nitrophenol, 4-nitrophenol, pentachlorophenol, phenol, toluene, dimethylsulfoxide, lead nitrate, cadmium chloride, sodium chloride, menadione, ethidium bromide, serine hydroxamate, acetate, propionate, hydrogen peroxide, puromycin, mercury chloride, 2,4-dichloroaniline, propanol, butanol, isopropanol, methylene chloride, Triton X100, acrylamide, methyl viologen, mitomycin C, xylene and ultraviolet irradiation.

6. The method of claim 1 or 2 wherein the environmental result stimulates a stress response selected from the group consisting of:

(i) protein damage time alters the action of rpoH or its gene product, (ii) oxidative damage that alters the action of oxyR or its gene product, (iii) oxidative damage that alters the action of soxRS or their respective gene products, (iv) membrane damage that alters the action of fadR or its gene product, (v) amine acid starvation that alters the action relA and spoT or their respective gene products, (vi) carbon starvation that alters the action of cya and crp or their respective gene products, (vii) phosphate starvation that alters the action of phoB, phoM, phoR, and phoU or their respective gene products;

(viii) nitrogen starvation that alters the action of glnB, glaD, glnG, and glnL or their respective gene products;

(ix) the universal stress response that alters the action of its regulators;

(x) the stationary phase response that alters the action of rpoS or its gene product; and (xi) DNA damage that alters the action of lexA or recA or their respective gene products.

7. The method of claim 1 or 2 wherein the transformed detector *E. coli* is in the log phase when exposed to the environmental insult.

8. A transformed bioluminescent *E coli capable of an increase in bioluminescence upon exposure to a sublethal level of environmental insult, the transformed bioluminescent E. coli* comprising:

(a) a stress inducible promoter sequence wherein the promoter sequence is responsive to a regulatory circuit; and (b) an expressible heterologous luxCDABE gone complex under the control the stress inducible promoter sequence.

9. The transformed bioluminescent *E. coli* of claim 8 further comprising a tolC$^-$ mutation wherein the mutation alters the permeability of the cell envelope of the *E. coli* to a hydrophobic environmental insult.

10. A method of detecting the presence of a environmental insult comprising:

(a) exposing a transformed detector *E. coli* to a sublethal environmental insult, the transformed detector *E. coli* being genetically engineered to contain an expressible heterologous luxCDABE gone complex under the control of a stress-inducible promoter sequence wherein the promoter sequence is responsive to a regulatory circuit; and (b) measuring an increase in luminescence of the transformed detector E. coli, the increase indicating the presence of an environmental insult.

11. *E. coli* selected from the group consisting of:

(i) TV1076 having ATCC Number 69314 comprising a tolC$^-$ mutation and an expressible heterologous lux gene complex under the control of a grpE stress inducible promoter sequence;

(ii) WM1302 having ATCC Number 69316 comprising a tolC$^-$ mutation and an expressible heterologous lux gene complex under the control of a dnaK stress inducible promoter sequence;

(iii) TV1060 having ATCC Number 69142 comprising an expressible heterologous lux gene complex under control of a grpE stress inducible promoter sequence;

(iv) TV1061 having ATCC Number 69315 comprising an expressible heterologous lux gene complex under control of a grpE stress inducible promoter sequence;

(v) WM1021 having ATCC Number 69141 comprising an expressible heterologous lux gene complex under control of a dnaK stress inducible promoter sequence;

(vi) WM1026 having ATCC Number 69143 comprising an expressible heterologous lux gene complex under control of a dnaK stress inducible promoter sequence; and (vii) WM1202 having ATCC Number 69313 comprising an expressible heterologous lux gene complex under control of a dnaK stress inducible promoter sequence.

12. A nucleic acid molecule, comprising:

(a) a stress inducible promoter sequence wherein said promoter sequence is responsive to a regulatory circuit; and (b) an expressible bacterial luxCDABE gene complex under control of said promoter sequence.

13. The nucleic acid molecule according to claim 12 wherein the stress inducible promoter sequence is selected from the group consisting of groEL, dnaK, grpE, phoA, glnA, lon, lysU, rpoD, clpB, clpP, uspA, katG, uvrA, frdA, micF, fabA, lac, his, sodA, sodB, soi-28, recA, xthA, and narG.

* * * * *